US011096584B2

(12) United States Patent
Mercader et al.

(10) Patent No.: US 11,096,584 B2
(45) Date of Patent: Aug. 24, 2021

(54) SYSTEMS AND METHODS FOR DETERMINING LESION DEPTH USING FLUORESCENCE IMAGING

(71) Applicants: The George Washington University, Washington, DC (US); 460MEDICAL, INC., Cambridge, MA (US)

(72) Inventors: Marco A. Mercader, Arlington, VA (US); Narine Sarvazyan, Potomac, MD (US); Terrance J. Ransbury, Chapel Hill, NC (US); Kenneth C. Armstrong, Cary, NC (US); Omar Amirana, Cambridge, MA (US)

(73) Assignees: The George Washington University, Washington, DC (US); 460Medical, Inc., Cambridge, MA (US)

( * ) Notice: Subject to any disclaimer, the term of this patent is extended or adjusted under 35 U.S.C. 154(b) by 318 days.

(21) Appl. No.: 14/541,991

(22) Filed: Nov. 14, 2014

(65) Prior Publication Data

US 2015/0196202 A1     Jul. 16, 2015

Related U.S. Application Data

(60) Provisional application No. 61/904,018, filed on Nov. 14, 2013.

(51) Int. Cl.
*A61B 5/00* (2006.01)
*A61B 18/00* (2006.01)
(Continued)

(52) U.S. Cl.
CPC ............ *A61B 5/0071* (2013.01); *A61B 1/043* (2013.01); *A61B 5/0044* (2013.01);
(Continued)

(58) Field of Classification Search
None
See application file for complete search history.

(56) References Cited

U.S. PATENT DOCUMENTS

| 4,024,873 A | 5/1977 | Antoshkiw et al. |
| 4,619,247 A | 10/1986 | Inoue et al. |
| (Continued) | | |

FOREIGN PATENT DOCUMENTS

| CN | 1289239 | 3/2001 |
| CN | 1764419 | 4/2006 |
| (Continued) | | |

OTHER PUBLICATIONS

Anderson et al. "Real-time spectroscopic assessment of thermal damage: implications for radiofrequency ablation". J Gastrointest Surg. 2004; 8: 660-669.
(Continued)

*Primary Examiner* — Keith M Raymond
*Assistant Examiner* — Helene Bor
(74) *Attorney, Agent, or Firm* — Greenberg Traurig, LLP; David J. Dykeman; Roman Fayerberg

(57) ABSTRACT

Systems, catheter and methods for treating Atrial Fibrillation (AF) are provided, which are configure to illuminate a heart tissue having a lesion site; obtain a mitochondrial nicotinamide adenine dinucleotide hydrogen (NADH) fluorescence intensity from the illuminated heart tissue along a first line across the lesion site; create a 2-dimensional (2D) map of the depth of the lesion site along the first line based on the NADH fluorescence intensity; and determine a depth of the lesion site at a selected point along the first line from the 2D map, wherein a lower NADH fluorescence intensity corresponds to a greater depth in the lesion site and a higher NADH fluorescence intensity corresponds to an unablated
(Continued)

INTERLESION GAP tissue. The process may be repeated to create a 3 dimensional map of the depth of the lesion.

21 Claims, 19 Drawing Sheets

(51) Int. Cl.
*A61B 5/02* (2006.01)
*A61B 18/02* (2006.01)
*A61B 18/12* (2006.01)
*A61B 90/30* (2016.01)
*A61B 1/04* (2006.01)
*A61B 90/00* (2016.01)

(52) U.S. Cl.
CPC ........ *A61B 5/0084* (2013.01); *A61B 5/02028* (2013.01); *A61B 18/00* (2013.01); *A61B 90/30* (2016.02); *A61B 18/02* (2013.01); *A61B 18/12* (2013.01); *A61B 2018/00351* (2013.01); *A61B 2090/3614* (2016.02); *A61B 2576/023* (2013.01)

(56) References Cited

U.S. PATENT DOCUMENTS

| | | | |
|---|---|---|---|
| 5,074,306 A | 12/1991 | Green et al. | |
| 5,187,572 A | 2/1993 | Nakamura et al. | |
| 5,350,375 A | 9/1994 | Deckelbaum et al. | |
| 5,419,323 A | 5/1995 | Kittrell et al. | |
| 5,421,337 A | 6/1995 | Richards-Kortum et al. | |
| 5,507,287 A | 4/1996 | Palcic et al. | |
| 5,590,660 A | 1/1997 | MacAulay et al. | |
| 5,749,830 A | 5/1998 | Kaneko et al. | |
| 5,885,258 A | 3/1999 | Sachdeva et al. | |
| 6,064,069 A | 5/2000 | Nakano et al. | |
| 6,124,597 A * | 9/2000 | Shehada | A61B 5/0075 600/320 |
| 6,174,291 B1 | 1/2001 | McMahon et al. | |
| 6,178,346 B1 | 1/2001 | Amundson et al. | |
| 6,208,886 B1 * | 3/2001 | Alfano | A61B 5/0073 250/341.1 |
| 6,219,566 B1 | 4/2001 | Weersink et al. | |
| 6,343,228 B1 | 1/2002 | Qu | |
| 6,450,971 B1 | 9/2002 | Andrus et al. | |
| 6,516,217 B1 | 2/2003 | Tsujita | |
| 6,825,928 B2 * | 11/2004 | Liu | A61B 5/0059 600/317 |
| 6,937,885 B1 | 8/2005 | Lewis et al. | |
| 6,975,898 B2 | 12/2005 | Seibel | |
| 6,975,899 B2 * | 12/2005 | Faupel | A61B 5/0071 600/407 |
| 6,979,290 B2 | 12/2005 | Mourlas et al. | |
| 7,235,045 B2 * | 6/2007 | Wang | A61B 1/00009 600/109 |
| 7,534,204 B2 | 5/2009 | Starksen et al. | |
| 7,539,530 B2 | 5/2009 | Caplan et al. | |
| 7,596,404 B2 | 9/2009 | Maier et al. | |
| 7,598,088 B2 | 10/2009 | Balas | |
| 7,640,046 B2 | 12/2009 | Pastore | |
| 7,662,152 B2 | 2/2010 | Sharareh et al. | |
| 7,729,750 B2 * | 6/2010 | Tromberg | A61B 5/0073 600/476 |
| 7,837,676 B2 | 11/2010 | Sinelnikov et al. | |
| 7,930,016 B1 | 4/2011 | Saadat | |
| 7,974,683 B2 | 7/2011 | Balaset et al. | |
| 8,024,027 B2 | 9/2011 | Freeman et al. | |
| 8,050,746 B2 | 11/2011 | Saadat et al. | |
| 8,078,266 B2 | 12/2011 | Saadat et al. | |
| 8,123,742 B2 | 2/2012 | Berger | |
| 8,131,350 B2 | 3/2012 | Saadat et al. | |
| 8,137,333 B2 | 3/2012 | Saadat et al. | |
| 8,144,966 B2 | 3/2012 | Provenzano et al. | |
| 8,175,688 B2 | 5/2012 | Lewis et al. | |
| 8,188,446 B2 | 5/2012 | Ohno | |
| 8,219,183 B2 | 7/2012 | Mashke et al. | |
| 8,221,310 B2 | 7/2012 | Saadat et al. | |
| 8,235,985 B2 | 8/2012 | Saadat et al. | |
| 8,309,346 B2 * | 11/2012 | Zuckerman | A61B 5/14546 356/364 |
| 8,333,012 B2 | 12/2012 | Rothe et al. | |
| 8,374,682 B2 | 2/2013 | Freeman et al. | |
| 8,417,321 B2 | 4/2013 | Saadat et al. | |
| 8,419,613 B2 | 4/2013 | Saadat et al. | |
| 8,460,285 B2 | 6/2013 | Wang et al. | |
| 8,463,366 B2 | 6/2013 | Freeman et al. | |
| 8,500,730 B2 | 8/2013 | Lee et al. | |
| 8,882,697 B2 | 11/2014 | Celermajer et al. | |
| 8,929,973 B1 * | 1/2015 | Webb | A61N 5/0622 600/476 |
| 9,008,746 B2 | 4/2015 | Pastore et al. | |
| 9,014,789 B2 | 4/2015 | Mercader et al. | |
| 9,084,611 B2 | 7/2015 | Amirana et al. | |
| 9,220,411 B2 * | 12/2015 | Hillman | A61B 5/0059 |
| 9,233,241 B2 | 1/2016 | Long | |
| 9,277,865 B2 | 3/2016 | Yamaguchi et al. | |
| 10,076,238 B2 | 9/2018 | Amirana et al. | |
| 10,143,517 B2 | 12/2018 | Ransbury et al. | |
| 10,568,535 B2 * | 2/2020 | Roberts | A61B 5/0077 |
| 10,682,179 B2 | 6/2020 | Ransbury et al. | |
| 10,716,462 B2 | 7/2020 | Amirana et al. | |
| 10,722,301 B2 | 7/2020 | Amirana et al. | |
| 10,736,512 B2 | 8/2020 | Mercader et al. | |
| 10,779,904 B2 | 9/2020 | Ransbury et al. | |
| 2002/0042556 A1 | 4/2002 | Sugimoto et al. | |
| 2002/0123666 A1 | 9/2002 | Matsumoto | |
| 2003/0028188 A1 | 2/2003 | Paddock et al. | |
| 2003/0120142 A1 | 6/2003 | Dubuc et al. | |
| 2004/0097788 A1 | 5/2004 | Mourlas et al. | |
| 2004/0215310 A1 | 10/2004 | Amirana | |
| 2005/0043637 A1 | 2/2005 | Caplan et al. | |
| 2005/0119523 A1 | 6/2005 | Starksen et al. | |
| 2005/0197530 A1 | 9/2005 | Wallace et al. | |
| 2005/0197623 A1 | 9/2005 | Leeflang et al. | |
| 2005/0228452 A1 | 10/2005 | Mourlas et al. | |
| 2005/0283195 A1 | 12/2005 | Pastore et al. | |
| 2006/0013454 A1 | 1/2006 | Flewelling et al. | |
| 2006/0025760 A1 | 2/2006 | Podhajsky | |
| 2006/0089636 A1 | 4/2006 | Christopherson et al. | |
| 2006/0184048 A1 | 8/2006 | Saadat | |
| 2006/0229594 A1 * | 10/2006 | Francischelli | A61N 7/02 606/27 |
| 2007/0015964 A1 | 1/2007 | Eversull et al. | |
| 2007/0016079 A1 | 1/2007 | Freeman et al. | |
| 2007/0016130 A1 | 1/2007 | Leeflang et al. | |
| 2007/0049827 A1 | 3/2007 | Donaldson et al. | |
| 2007/0083217 A1 | 4/2007 | Eversull et al. | |
| 2007/0167828 A1 | 7/2007 | Saadat | |
| 2007/0270717 A1 | 11/2007 | Tang et al. | |
| 2007/0270789 A1 | 11/2007 | Berger | |
| 2007/0276259 A1 | 11/2007 | Okawa et al. | |
| 2007/0287886 A1 | 12/2007 | Saadat | |
| 2007/0293724 A1 | 12/2007 | Saadat et al. | |
| 2008/0009747 A1 | 1/2008 | Saadat et al. | |
| 2008/0015569 A1 | 1/2008 | Saadat et al. | |
| 2008/0033241 A1 | 2/2008 | Peh et al. | |
| 2008/0058650 A1 | 3/2008 | Saadat et al. | |
| 2008/0058785 A1 | 3/2008 | Boyden et al. | |
| 2008/0058786 A1 | 3/2008 | Boyden et al. | |
| 2008/0097476 A1 | 4/2008 | Peh et al. | |
| 2008/0101677 A1 | 5/2008 | Mashke et al. | |
| 2008/0103355 A1 | 5/2008 | Boyden et al. | |
| 2008/0119694 A1 | 5/2008 | Lee | |
| 2008/0183036 A1 | 7/2008 | Saadat et al. | |
| 2008/0212867 A1 * | 9/2008 | Provenzano | A61B 5/0059 382/133 |
| 2008/0214889 A1 | 9/2008 | Saadat et al. | |
| 2008/0228032 A1 | 9/2008 | Starksen et al. | |
| 2008/0275300 A1 | 11/2008 | Rothe et al. | |
| 2008/0281293 A1 | 11/2008 | Peh et al. | |
| 2009/0012367 A1 | 1/2009 | Chin et al. | |
| 2009/0030276 A1 | 1/2009 | Saadat et al. | |
| 2009/0030412 A1 | 1/2009 | Willis et al. | |

(56) References Cited

U.S. PATENT DOCUMENTS

| | | |
|---|---|---|
| 2009/0054803 A1 | 2/2009 | Saadat et al. |
| 2009/0062790 A1 | 3/2009 | Malchano et al. |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0204069 A1 | 8/2009 | Hirszowicz et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0292211 A1 | 11/2009 | Lin et al. |
| 2009/0299363 A1 | 12/2009 | Saadat et al. |
| 2010/0022832 A1 | 1/2010 | Makiyama |
| 2010/0081127 A1 | 4/2010 | Maier et al. |
| 2010/0081948 A1 | 4/2010 | Pastore et al. |
| 2010/0084563 A1 | 4/2010 | Ohno |
| 2011/0042580 A1 | 2/2011 | Wilson et al. |
| 2011/0082451 A1 | 4/2011 | Melsky et al. |
| 2011/0117025 A1 | 5/2011 | Dacosta et al. |
| 2011/0224494 A1 | 9/2011 | Piskun et al. |
| 2011/0230903 A1 | 9/2011 | Bertolero |
| 2011/0275932 A1* | 11/2011 | Leblond ............... A61B 5/0062 600/425 |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0215112 A1 | 8/2012 | Lewis et al. |
| 2012/0220999 A1 | 8/2012 | Long |
| 2012/0259263 A1 | 10/2012 | Celermajer et al. |
| 2012/0326055 A1 | 12/2012 | Wilson et al. |
| 2013/0006116 A1 | 1/2013 | Kim et al. |
| 2013/0030425 A1 | 1/2013 | Stewart et al. |
| 2013/0079645 A1 | 3/2013 | Amirana et al. |
| 2013/0102862 A1* | 4/2013 | Mercader ............ A61B 5/1459 600/317 |
| 2013/0107002 A1 | 5/2013 | Kikuchi |
| 2013/0137949 A1 | 5/2013 | Freeman et al. |
| 2013/0237841 A1 | 9/2013 | Freeman et al. |
| 2013/0281920 A1 | 10/2013 | Hawkins et al. |
| 2013/0310680 A1* | 11/2013 | Werahera ............ A61B 5/0035 600/411 |
| 2014/0031802 A1 | 1/2014 | Melsky |
| 2014/0058246 A1 | 2/2014 | Boveja et al. |
| 2014/0316280 A1 | 10/2014 | Mueller et al. |
| 2014/0357956 A1 | 12/2014 | Salahieh et al. |
| 2014/0378843 A1* | 12/2014 | Valdes .................. G02B 21/36 600/476 |
| 2015/0099979 A1 | 4/2015 | Caves et al. |
| 2015/0141847 A1 | 5/2015 | Sarvazyan |
| 2015/0164332 A1 | 6/2015 | Mercader et al. |
| 2015/0216398 A1* | 8/2015 | Yang .................... G01J 3/0208 600/109 |
| 2015/0327753 A1 | 11/2015 | Amirana et al. |
| 2015/0346100 A1* | 12/2015 | Racowsky ......... G01N 21/6408 435/34 |
| 2016/0051321 A1 | 2/2016 | Salahieh et al. |
| 2016/0120599 A1 | 5/2016 | Amirana et al. |
| 2016/0120602 A1 | 5/2016 | Ransbury et al. |
| 2016/0143522 A1 | 5/2016 | Ransbury et al. |
| 2017/0014202 A1 | 1/2017 | Ransbury et al. |
| 2017/0135559 A1 | 5/2017 | Horrisberger et al. |
| 2018/0263476 A1 | 9/2018 | Amirana et al. |
| 2019/0053849 A1 | 2/2019 | Ransbury et al. |
| 2020/0008681 A1 | 1/2020 | Sarvazyan |
| 2020/0352425 A1 | 11/2020 | Amirana et al. |
| 2020/0352644 A1 | 11/2020 | Ransbury et al. |
| 2020/0352645 A1 | 11/2020 | Amirana et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 106028914 | 10/2016 |
| DE | 10200521205 | 11/2006 |
| DE | 102011083522 | 3/2013 |
| EP | 2691041 | 2/2014 |
| EP | 2889013 A1 | 7/2015 |
| JP | 60182928 A | 9/1985 |
| JP | 63-262613 | 10/1988 |
| JP | 10150177 A | 6/1998 |
| JP | 2006158546 A | 6/2006 |
| JP | 2011212423 A | 10/2011 |
| NL | 2002010 | 10/2009 |
| WO | 1997/037622 | 10/1997 |
| WO | 1999013934 A1 | 3/1999 |
| WO | 2001001854 | 1/2001 |
| WO | 2001072214 | 10/2001 |
| WO | 2003092520 A1 | 11/2003 |
| WO | 2004028353 A2 | 4/2004 |
| WO | 2006028824 | 3/2006 |
| WO | 2007109554 | 9/2007 |
| WO | 2007127228 A2 | 11/2007 |
| WO | 2008/028149 A2 | 3/2008 |
| WO | 2008114748 | 9/2008 |
| WO | 2008154578 | 12/2008 |
| WO | 2010075450 | 7/2010 |
| WO | 2011025640 | 3/2011 |
| WO | 2011113162 | 9/2011 |
| WO | 2012049621 A1 | 4/2012 |
| WO | 2012067682 A1 | 5/2012 |
| WO | 2013068885 A1 | 5/2013 |
| WO | 2013116316 | 8/2013 |
| WO | 2013116316 A1 | 8/2013 |
| WO | 2013169340 A1 | 11/2013 |
| WO | 2014028770 | 2/2014 |
| WO | 2015073871 | 5/2015 |
| WO | 2016073492 A1 | 5/2016 |
| WO | 2016/086160 | 6/2016 |

OTHER PUBLICATIONS

Asfour et al, "Signal decomposition of transmembrane voltage-sensitive dye fluorescence using a multiresolution wavelet analysis" IEEE Trans Biomed Eng. 2011; 58: 2083-2093.

Boersma et al,."Pulmonary vein isolation by duty-cycled bipolar and unipolar radiofrequency energy with a multielectrode ablation catheter". Heart Rhythm5:1635-1642, 2008.

Buch et al. "Epicardial catheter ablation of atrial fibrillation." Minerva Med. 2009; 100: 151-157.

Chance et al, "Fluorescence measurements of mitochondrial pyridine nucleotide in aerobiosis and anaerobiosis" Nature. 1959; 184: 931-4.

Coremans et al, "Pretransplantation assessment of renal viability with NADH fluorimetry", Kidney International, vol. 57, (2000), pp. 671-683.

D'Avila A. "Epicardial catheter ablation of ventricular tachycardia." Heart Rhythm. 2008; 5: S73-5.

Demos et al, "Real time assessment of RF cardiac tissue ablation with optical spectroscopy", Opt Express. 2008; 16: 15286-15296.

Dickfeld et al, "Characterization of Radiofrequency Ablation Lesions With Gadolinium-Enhanced Cardiovascular Magnetic Resonance Imaging" J Am Coll Cardiol. 2006; 47: 370-378.

Dukkipati et al, "Visual balloon-guided point-by-point ablation: reliable, reproducible, and persistent pulmonary vein isolation", Circ Arrhythm Electrophysiol. 2010; 3: 266-273.

Dumas et al, "Myocardial electrical impedance as a predictor of the quality of RF-induced linear lesions." Physiol Meas. 2008; 29: 1195-1207.

Fleming et al, "Real-time monitoring of cardiac redio-frequency ablation lesion formation using an optical coherence tomography forward-imaging catheter", Journal of Biomedical Optics, May/Jun. 2010, vol. 15(3).

(56) References Cited

OTHER PUBLICATIONS

Fleming et al, "Toward guidance of epicardial cardiac radiofrequency ablation therapy using optical coherence tomography" J Biomed Opt. 2010; 15: 041510.
Girard et al, "Contrast-enhanced C-arm CT evaluation of radiofrequency ablation lesions in the left ventricle", JACC Cardiovasc Imaging. 2011; 4: 259-268.
Grimard et al, "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Head Circ Physiol, May 2012; 302(10): H2131-H2138.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.

Roger et al, "American Heart Association Stastics Committee and Stroke Subcommittee. Heart disease and stroke statistics—2011 update; a report from American Heart Association", Circulation 2011; 123: e18-e209.
Sosa et al, "Epicardial mapping and ablation techniques to control ventricular tachycardia". J Cardiovasc Electrophysiol. 2005; 16: 449-452.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Van Haesendonck C, Sinnaeve A, Willems R, Vandenbulcke F, Stroobandt R, ."Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
International Search Report dated Dec. 3, 2012 for PCT/US2012/056771.
Office Action issued in U.S. Appl. No. 13/624,902 dated Oct. 2, 2014.
Office Action issued in U.S. Appl. No. 13/624,899 dated Oct. 2, 2014.
International Search Report dated Feb. 19, 2015 for PCT/US2014/065774.
Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).
Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).
Cancio et al., "Hyperspectral Imaging: A New Approach to the Diagnosis of Hemorrhagic Shock", The Journal of Trauma, 2006, vol. 60, No. 5: 1087-1095.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Vo-Dinh et al., "A Hyperspectral Imaging System for In Vivo Optical Diagnostics", IEEE Engineering in Medicine and Biology Magazine, pp. 40-49, Sep./Oct. 2004.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
International Search Report dated Feb. 12, 2015 for PCT/US2014/066660.
Office Action in U.S. Appl. No. 14/689,475 dated Apr. 6, 2016.
Office Action in U.S. Appl. No. 14/931,262 dated Apr. 20, 2018.
Office Action in U.S. Appl. No. 14/622,477 dated Jun. 5, 2018.
Office Action in U.S. Appl. No. 14/549,057 dated Jun. 15, 2018.
European Search Report completed Jun. 8, 2018 for EP 15 86 3645.
Office Action in U.S. Appl. No. 14/931,325 dated Mar. 22, 2018.
Office Action in U.S. Appl. No. 14/952,048 dated Aug. 27, 2018.
Office Action in U.S. Appl. No. 14/931,262 dated Aug. 28, 2018.
Office Action in U.S. Appl. No. 15/986,970 dated Sep. 17, 2018.
Office Action in U.S. Appl. No. 14/549,057 dated Dec. 13, 2018.
Office Action in U.S. Appl. No. 14/622,477 dated Dec. 19, 2018.
Office Action in U.S. Appl. No. 15/986,970 dated Jan. 10, 2019.
Office Action in U.S. Appl. No. 14/931,262 dated Jan. 11, 2019.
Office Action in U.S. Appl. No. 16/167,933 dated Jan. 11, 2019.
Office Action in U.S. Appl. No. 14/952,048 dated Mar. 1, 2019.
Office Action in U.S. Appl. No. 14/919,004 dated Apr. 4, 2019.
Office Action in U.S. Appl. No. 14/931,262 dated Aug. 22, 2019.
Office Action in U.S. Appl. No. 14/622,477 dated Sep. 5, 2019.
Office Action in U.S. Appl. No. 15/986,970 dated Sep. 16, 2019.
Office Action in U.S. Appl. No. 16/167,933 dated Sep. 25, 2019.

(56) References Cited

OTHER PUBLICATIONS

Extended European Search Report dated Feb. 20, 2019 for EP 16 828 397.6.
Office Action in U.S. Appl. No. 14/952,048 dated Oct. 31, 2019.
Office Action in U.S. Appl. No. 14/919,004 dated Jan. 7, 2020.
Office Action in U.S. Appl. No. 14/952,048 dated Jul. 8, 2020.
Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.
Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May, 1990.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Smith, S., et al., "Imaging Appearances Following Thermal Ablation", Clinical Radiology, vol. 63, Issue 1, pp. 1-11, Jan. 2008.
Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swift, L.M., et al., "Properties of Blebbistatin for Cardiac Optical Mapping and Other Imaging Applications", European Journal of Physiology, vol. 464, Issue 5, pp. 503-512, Nov. 2012.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.
European Search Report completed May 26, 2015 for EP 12 83 4435.
International Search Report dated Jan. 19, 2016 for PCT/US2015/058824.
Office Action in U.S. Appl. No. 14/689,475 dated Aug. 23, 2017.
Office Action in U.S. Appl. No. 14/622,477 dated Oct. 5, 2017.
Swift, Luther Mitchell, "Real-Time Visualization of Cardiac Ablation Lesions Using Endogenous NADH Fluorescence and Reflected Light", A dissertation submitted to The Faculty of The Columbian College of Arts and Sciences of The George Washington University in partial fulfillment of the requirements for the degree of Doctor of Philosophy, Jul. 23, 2013.

\* cited by examiner

FIG. 4C
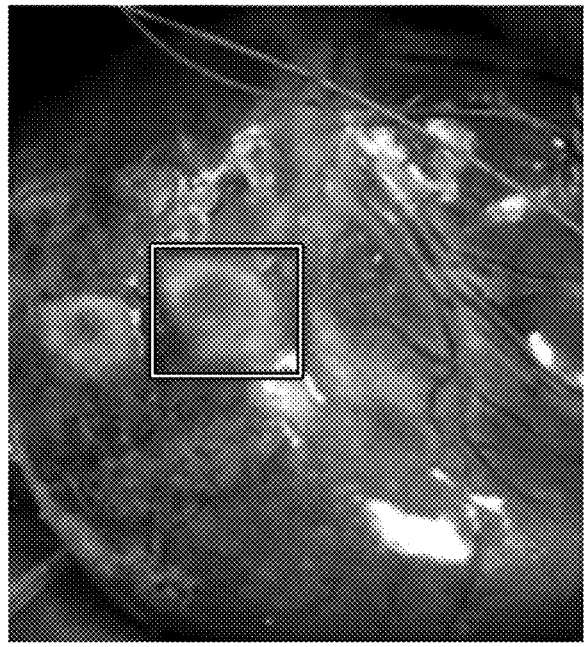
FIG. 4D
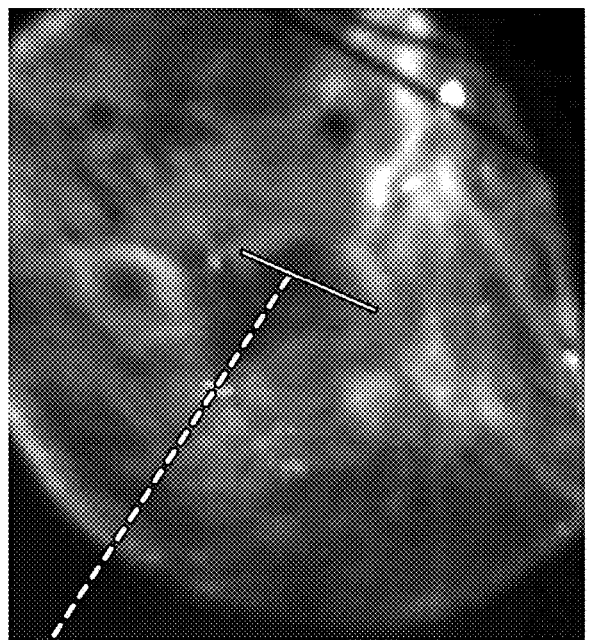
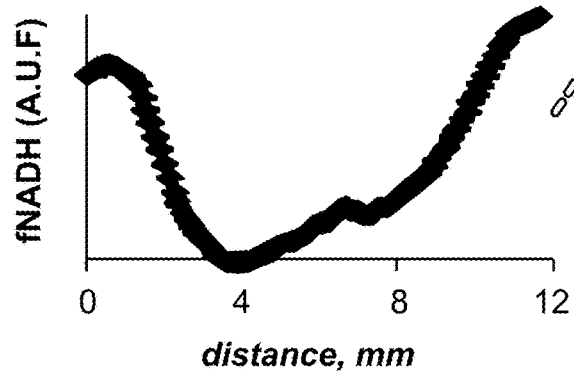
FIG. 4E
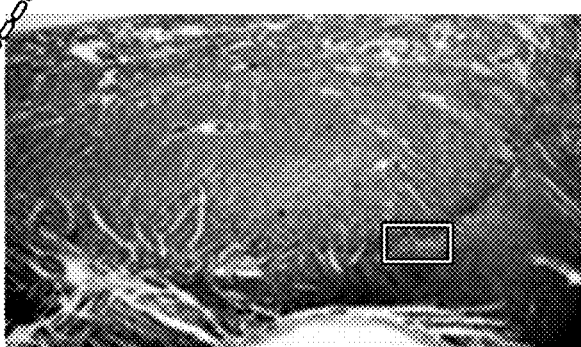
FIG. 4F

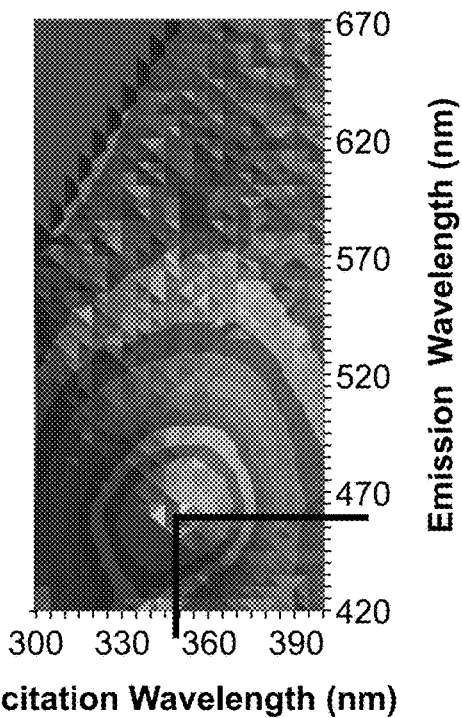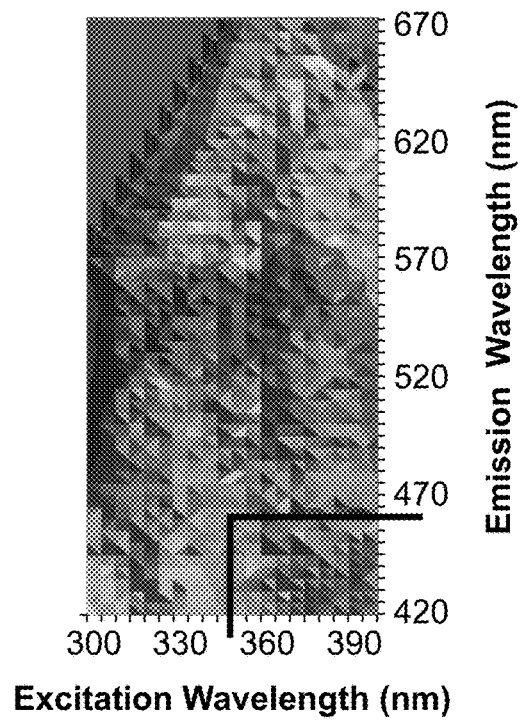
FIG. 5A
FIG. 5B
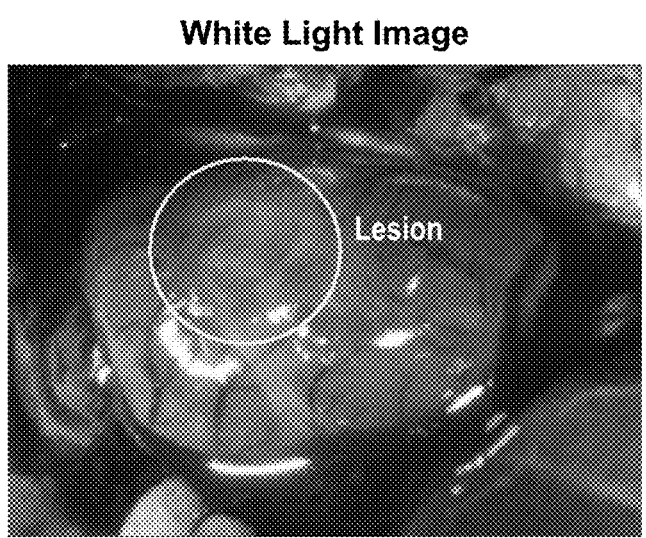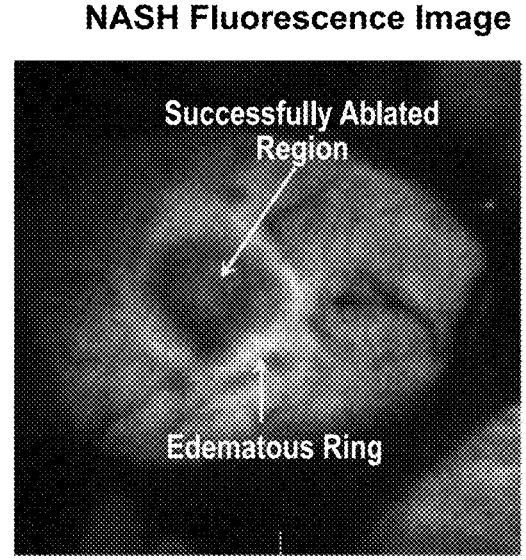
FIG. 6A
FIG. 6B

Epicardial NADH flourescense (fNADH) crrelates with lesion diameter

CRYOLESION

RADIOFREQUENCY

SYSTEMS AND METHODS FOR DETERMINING LESION DEPTH USING FLUORESCENCE IMAGING

RELATED APPLICATIONS

This application claims the benefit of and priority to U.S. Provisional Application Ser. No. 61/904,018, filed on Nov. 14, 2013, which is incorporated herein by reference in its entirety.

FIELD

The present disclosure generally relates to medical procedures where ablation energy is applied to the body to form therapeutic lesions. In particular, the present disclosure relates to systems and methods for imaging lesions and tissue to determine lesion depth.

BACKGROUND

Atrial fibrillation (AF) is the most common sustained arrhythmia in the world, which currently affects millions of people. In the United States, AF is projected to affect 10 million people by the year 2050. AF is associated with increased mortality, morbidity, and an impaired quality of life, and is an independent risk factor for stroke. The substantial lifetime risk of developing AF underscores the public heath burden of the disease, which in the U.S. alone amounts to an annual treatment cost exceeding $7 billion.

Most episodes in patients with AF are known to be triggered by focal electrical activity originating from within muscle sleeves that extend into the Pulmonary Veins (PV). Atrial fibrillation may also be triggered by focal activity within the superior vena cava or other atrial structures, i.e. other cardiac tissue within the heart's conduction system. These focal triggers can also cause atrial tachycardia that is driven by reentrant electrical activity (or rotors), which may then fragment into a multitude of electrical wavelets that are characteristic of atrial fibrillation. Furthermore, prolonged AF can cause function alterations in cardiac cell membranes and these changes further perpetuate atrial fibrillation.

Radiofrequency ablation (RFA), laser ablation and cryo ablation are the most common technologies of catheter-based mapping and ablation systems used by physicians to treat atrial fibrillation. Physician uses a catheter to direct energy to either destroy focal triggers or to form electrical isolation lines isolating the triggers from the heart's remaining conduction system. The latter technique is commonly used in what is called pulmonary vein isolation (PVI). However, the success rate of the AF ablation procedure has remained relatively stagnant with estimates of recurrence to be as high as 30% to 50% one-year post procedure. The most common reason for recurrence after catheter ablation is one or more gaps in the PVI lines. The gaps are usually the result of ineffective or incomplete lesions that may temporarily block electrical signals during the procedure but heal over time and facilitate the recurrence of atrial fibrillation.

Therefore, there is a need in forming and verifying proper lesions, reduce fluoroscopy time, and reduce the rate of arrhythmia occurrence, thereby improving outcomes and reducing costs.

SUMMARY

According to some aspects of the present disclosure, there is provided a method for determining a depth of a lesion site that includes illuminating a heart tissue having a lesion site; obtaining a mitochondrial nicotinamide adenine dinucleotide hydrogen (NADH) fluorescence intensity from the illuminated heart tissue along a first line across the lesion site; creating a 2-dimensional (2D) map of the depth of the lesion site along the first line based on the NADH fluorescence intensity; and determining a depth of the lesion site at a selected point along the first line from the 2D map, wherein a lower NADH fluorescence intensity corresponds to a greater depth in the lesion site and a higher NADH fluorescence intensity corresponds to an unablated tissue.

In some embodiments, the method further comprises forming the lesion site in the heart tissue by ablation. The step of obtaining may comprise detecting the NADH fluorescence from the illuminated tissue; creating a digital image of the lesion site from the NADH fluorescence, the digital image comprising a plurality of pixels; and determining a NADH fluorescence intensity of the plurality of pixels along the line across the lesion site. In some embodiments, the method may further include distinguishing the lesion site and a healthy tissue in the digital image based on an amount of the NADH fluorescence from the lesion site and the healthy tissue; normalizing the digital image based on the NADH fluorescence intensity of pixels representative of the healthy tissue.

In some embodiments, the step of detecting comprises filtering the NADH fluorescence through a bandpass filter of between about 435 nm and 485 nm. In some embodiments, the healthy tissue has a lighter appearance and the lesion site has a darker appearance. The step of creating may comprise plotting the NADH fluorescence intensity along the line across the lesion site to create the 2D map of depth of the lesion site.

In some embodiments, the method further includes obtaining a NADH fluorescence intensity from the illuminated heart tissue along a second line across the lesion site; creating a 2D map of the depth of the lesion site along the second line based on the NADH fluorescence intensity; constructing a 3-dimensional (3D) image of the lesion site from the 2D map along the first line and the 2D map along the second line. In some embodiments, the steps of obtaining, creating and determining may be repeated multiple times along a perpendicular line across a width of the lesion site, each of the 2D maps of the depth being parallel to the first line along the length of the lesion site; and integrating each of the respective 2D maps of the depth of the lesion site on a perpendicular line to reconstruct a 3D image of the depth of the lesion site.

The step of determining may comprise applying a pixel gray scale ranging from completely black to completely white. The method may be used to analyze epicardial tissue, endocardial tissue, atrial tissue, and ventricular tissue.

In some embodiments, the illuminating step comprises illuminating the heart tissue with a laser generated UV light, wherein the laser generated UV light may have a wavelength of about 300 nm to about 400 nm.

According to some aspects of the present disclosure, there is provided a system for imaging heart tissue that includes an illumination device configured to illuminate a tissue having a lesion site to excite mitochondrial nicotinamide adenine dinucleotide hydrogen (NADH) in the tissue; an imaging device configured to detect NADH fluorescence from the illuminated tissue; and a controller in communication with the imaging device, the controller being programmed to obtain a NADH fluorescence intensity from the illuminated tissue along a first line across the lesion site; create a 2-dimensional (2D) map of the depth of the lesion site along the first line based on the NADH fluorescence intensity; and determine a depth of the lesion site at a selected point along the first line from the 2D map, wherein a lower NADH fluorescence intensity corresponds to a greater depth in the lesion site and a higher NADH fluorescence intensity corresponds to an unablated tissue.

According to some aspects of the present disclosure, there is provided a system for imaging heart tissue that includes a catheter having a distal region and a proximal region; a light source; an optical fiber extending from the light source to the distal region of the catheter to illuminate a tissue having a lesion site in proximity to the distal end of the catheter to excite mitochondrial nicotinamide adenine dinucleotide hydrogen (NADH) in the tissue; an image bundle for detecting a NADH fluorescence from the illuminated tissue; a camera connected to the image bundle, the camera being configured to receive the NADH fluorescence from the illuminated tissue and to generate a digital image of the illuminated tissue, the digital image comprising a plurality of pixels; and a controller in communication with the camera, the controller being configured to determine, from the digital image, a NAHD fluorescence intensity of the plurality of pixels along a first line across the lesion site, create a 2D map of a depth of the lesion site along the first line based on the NADH fluorescence intensity, and determine a depth of the lesion site at a selected point along the first line from the 2D map, wherein a lower NADH fluorescence intensity corresponds to a greater depth in the lesion site and a higher NADH fluorescence intensity corresponds to an unablated tissue

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 4C-4F show the depth analysis performed along a single line in accordance with the present disclosure.

FIG. 5A and FIG. 5B are a side-by-side plot of the emission wavelengths of healthy cardiac tissue (FIG. 5A) and ablated cardiac tissue (FIG. 5B).

FIG. 6A and FIG. 6B is a side-by side image comparison of a cardiac lesion illuminated under white light (FIG. 6A) and the NADH fluorescence due to illumination under UV light (FIG. 6B).

Figure 1A:
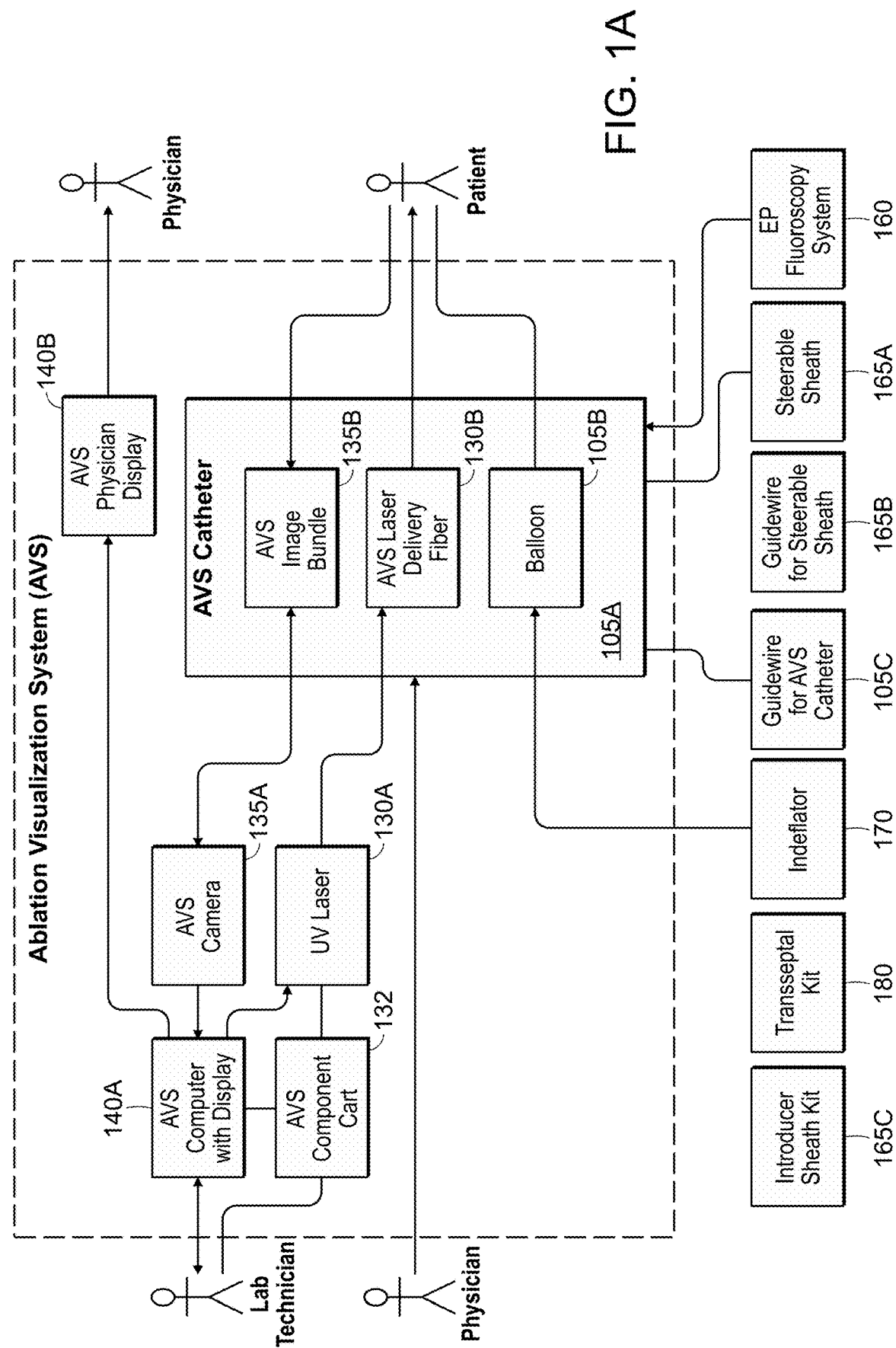
FIG. 1A is a system architecture diagram of an embodiment system of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure generally relates to medical procedures where radiofrequency, laser or cryo ablation energy is applied to the body to form therapeutic lesions. In particular, the present disclosure relates to systems and methods that can image cardiac lesions and tissue using nicotinamide adenine dinucleotide hydrogen (NADH) fluorescence (fNADH). The present systems and methods may be used during the treatment of Atrial Fibrillation (AF). In particular, the present disclosure relates to systems and methods for generating lesion depth maps by analyzing NADH fluorescence intensity data to determine the depth of lesions. In some embodiments, the present systems and methods may be employed to determine depth of lesions in heart tissue (endocardial, epicardial, atrial and ventricular tissue). However, the presently disclosed methods and systems may also be applicable for analyzing lesions in other tissue types. The lesions to be analyzed may be created by ablation during ablation procedure. In some embodiments, existing lesions, created by ablation or by other means, may also be analyzed using methods and systems disclosed herein.

According to aspects of the present disclosure, the fluorescence of endogenous NADH (fNADH) in heart tissue can be imaged in real-time to identify ablated and unablated areas. Gaps between ablated areas can be identified using the fNADH imaging and the gaps can then be ablated. The imaging can be performed during the ablation procedure and does not require additional chemicals, such as contrast agents, tracers or dyes.

In some embodiments, the intensity of fluorescence can be measured and plotted with the lowest fluorescence (darkest) corresponding to the deepest ablated lesions and the highest fluorescence (lightest) corresponding to the unablated or healthy tissue. Any levels of gray between the extremes of light and dark generally correspond to the degree of tissue lesion depth. The presently disclosed systems and methods can be used to determine lesion depth based on the pixel intensity obtained after ablating the tissue and imaging the tissue with a fNADH system. In some embodiments, the correlated depth data can be integrated into a 3D reconstruction of the lesion(s) giving the physician timely feedback about lesion geometry and quality. Thus, the present disclosure addresses the lack of lesion-quality feedback of today's known technologies and methods by providing depth-of-lesion information to the physician at the time of the procedure. For example, having depths information can be used for subsequent diagnosis and treatment. In performing ablation procedures, particularly pulmonary vein isolation procedures, at least one objective, among many, is to deliver ablation lesions that are deep enough to have durable results and enhance the success of the procedure. During the procedure it is optimum that the ablation lesions do not have gaps and each lesion has covered adequate depth. This is called transmural lesions, which means, without having damage to tissue outside the heart or perforates the heart; such that, the depth information is used at the time of a procedure by helping an operator perform better lesions that are deep enough to provide adequate results and more durable result. Further, the lesions that are produced can largely depend on the ablation tool that is used, RFA (standard vs irrigated), cryo (catheter vs balloon) and laser, they all produce different shape lesions. It is a challenge to overcome that the lesions produced depend on the ablation tool used, such that each ablation tool results in having a variable depth wherein some are deeper than others. In performing ablation procedures there are no minimal depth numbers, it can depend on several factors, such as the area being ablated, atrium is thinner than ventricle or some other factor. For example, a 2 mm depth may be perfect for atrial tissue but poor for ventricular tissue, however, each patient will have different thickness tissue and require specific attention.

As noted above, high quality and verifiable lesions can be at least some of the keys to the success of the ablation procedure and avoidance of recurrence. Quality lesions may be of adequate depth and cause cell necrosis completely from the endocardial surface to the epicardial surface of the heart (i.e. transmural) while minimizing damage to the non-cardiac structures beyond. However, the present disclosed mapping systems and other aspects of the systems and methods provide the feedback on the extent of cell injury caused by the ablation as well as actually verify the integrity of a lesion. Thus, the presently disclosed embodiments, among other things, address the lack of lesion-quality feedback of today's known technologies by providing lesion visualization as well as depth-of-lesion information to the physician at the time of the procedure.

Figure 1B:
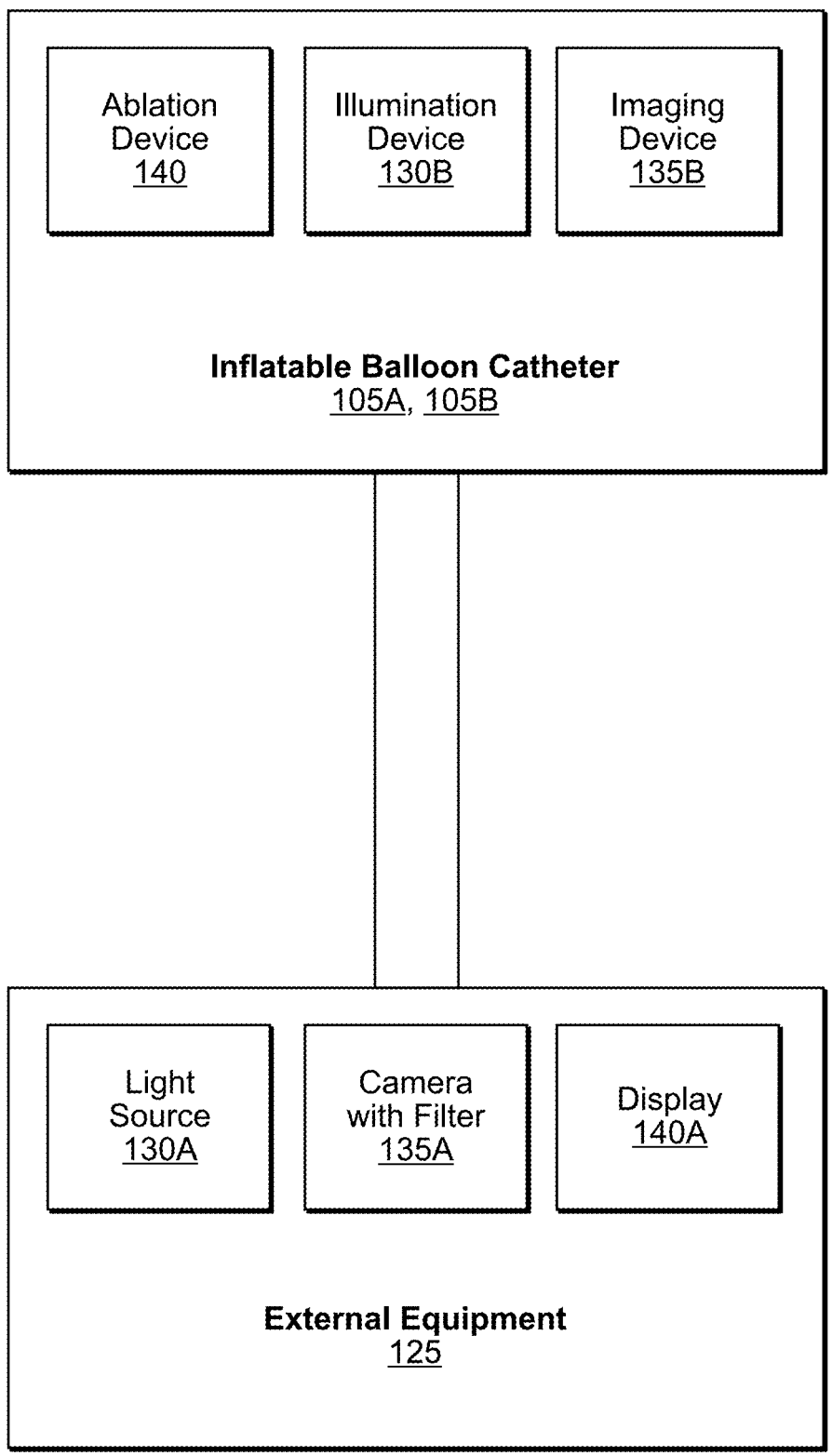
FIG. 1B is a block diagram of an embodiment system of the present disclosure.

In reference to FIG. 1A and FIG. 1B, the ablation visualization system (AVS) of the present disclosure can include a light source 130A, such as a UV laser, that is external to the body of a patient and light device or a light delivery fiber 130B for delivering light from the light source to within the body of the patient, a camera 135A with appropriate filtering, if necessary, and an image bundle 135B connected to the camera, and a computer system 140 having one or more displays 140A (for a technician) and 140B (for a physician) with image processing software on its processor or controller.

Figure 1C:
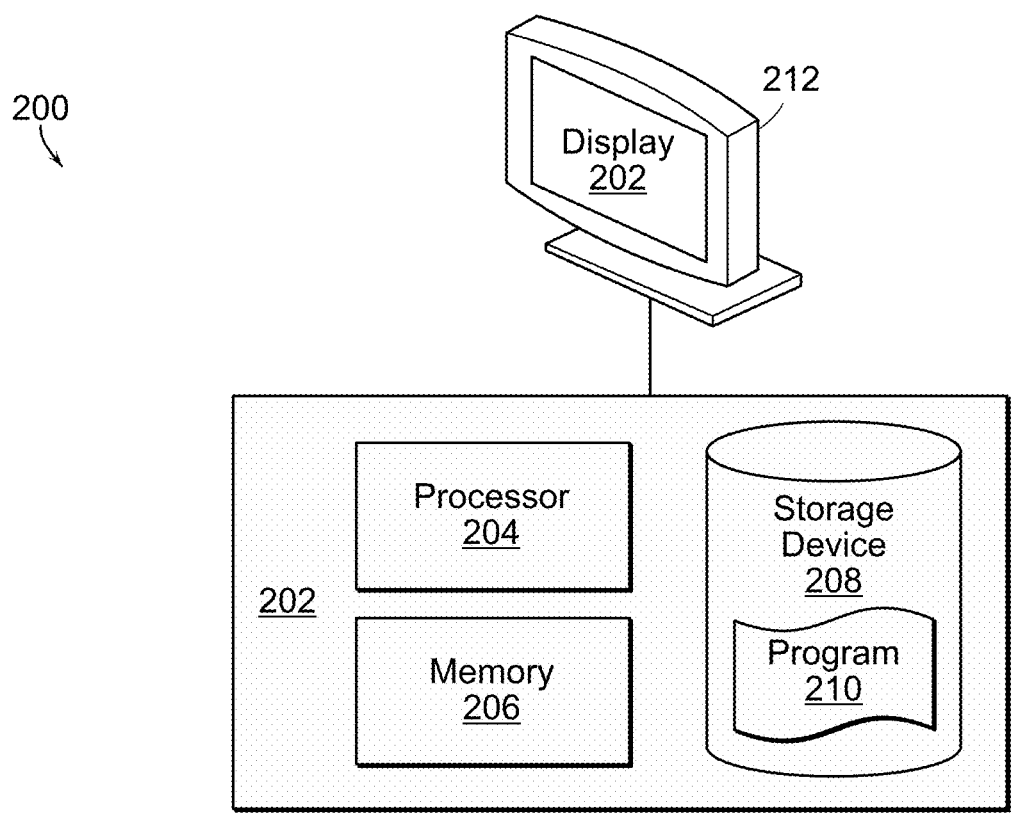
FIG. 1C is a diagram showing an exemplary computer system suitable for use with the methods and systems of the present disclosure.

FIG. 1C shows, by way of example, a diagram of a typical processing architecture, which may be used in connection with the methods and systems of the present disclosure. A computer processing device 200 can be coupled to display 212 for graphical output. Processor 202 can be a computer processor 204 capable of executing software. Typical examples can be computer processors (such as Intel® or AMD® processors), ASICs, microprocessors, and the like. Processor 204 can be coupled to memory 206, which can be typically a volatile RAM memory for storing instructions and data while processor 204 executes. Processor 204 may also be coupled to storage device 208, which can be a non-volatile storage medium, such as a hard drive, FLASH drive, tape drive, DVDROM, or similar device. Although not shown, computer processing device 200 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 200. Processor 204 may also be coupled to other type of computer-readable media, including, but are not limited to, an electronic, optical, magnetic, or other storage or transmission device capable of providing a processor, such as the processor 204, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C #, Visual Basic, Java, Python, Perl, and JavaScript.

Program 210 can be a computer program or computer readable code containing instructions and/or data, and can be stored on storage device 208. The instructions may comprise code from any computer-programming language, including, for example, C, C++, C #, Visual Basic, Java, Python, Perl, and JavaScript. In a typical scenario, processor 204 may load some or all of the instructions and/or data of program 210 into memory 206 for execution. Program 210 can be any computer program or process including, but not limited to web browser 166, browser application 164, address registration process 156, application 142, or any other computer application or process. Program 210 may include various instructions and subroutines, which, when loaded into memory 206 and executed by processor 204 cause processor 204 to perform various operations, some or all of which may effectuate the methods for managing medical care disclosed herein. Program 210 may be stored on any type of non-transitory computer readable medium, such as, without limitation, hard drive, removable drive, CD, DVD or any other type of computer-readable media.

It is possible the light source 130A may include a cart 132. In some embodiments, the system may further include a specialty catheter 105A comprising an inflatable balloon 105B. In some embodiments, the image bundle 135B and the light delivery fiber may extend from the outside of the catheter to a distal region of the catheter inside the balloon 105B. It is contemplated that there could be multiple components of each component added to the above disclosed system. The system may further include a guidewire for the catheter 105C, a EP Fluoroscopy System 160, a sterable sheath 165A, a guidewire for steerable sheath 165B, an introducer sheath kit 165C, an indeflator 170 and a trasseptal kit 180.

FIG. 1B is a block diagram of an exemplary system in accordance with the present disclosure. The AVS system includes external equipment 125 having a light source 130A, a camera 135A with appropriate filtering, if necessary, and a computer system (not shown) having one or more displays 140A with image processing software. The AVS system includes internal equipment including an ablation device 140, an illumination device 130B and an imaging device 135B, wherein the internal components are within an internal balloon 105B associated with a catheter 105A. It is noted that the internal equipment including the catheter 105A with an inflatable balloon catheter 105B is coupled to external equipment 125. In some embodiments, the illumination device 130B and an imaging device 135B may utilize a fiber-optic waveguide to pass the light to and from the treated tissue.

Still referring to FIG. 1A and FIG. 1B, the light source 130A may include a laser that is the source for illumination of the myocardium. The output wavelength of the laser may be within the target fluorophore fNADH, in this case) absorption range in order to induce fluorescence in the healthy myocardial cells. In some embodiments, the laser can be a UV laser.

According to some aspects of FIG. 1A and FIG. 1B, a laser generated UV light may provide much more power for illumination and its wavelength can be pure at whatever number of nanometers that may be required. Emitance of more than one wavelength may be problematic in that they may cause other molecules to fluoresce (other than NADH) and they may cause reflection in the reflectance range injecting image noise or worse, drowning out the NADH reflectance signal. There are sources of commercial lasers that can emit in a desired illumination band and they are available in many power settings near 50 to 200 mW and higher. The instant system, in some embodiments, uses a laser with adjustable power up to 150 mW.

The wavelength range on the illumination source may be bounded by the anatomy of interest, specifically choosing a wavelength that causes maximum NADH fluorescence but not too much collagen fluorescence, which is activated by only slightly longer wavelengths. In some embodiments, the laser has a wavelength from 300 nm to 400 nm. In some embodiments, the laser has a wavelength from 330 nm to 370 nm. In some embodiments, the laser has a wavelength from 330 nm to 355 nm. In some embodiments, 355 nm may be used because it was near the peak of NADH excitation and just below collagen excitation. The output power of the laser may be high enough to produce a recoverable fluorescence data, yet not so high as to induce cellular damage.

Still referring to FIG. 1A and FIG. 1B, the catheter 105A can be employed to perform many functions including, without limitations, vascular navigation, blood displacement, propagation of light from the light source 130A to the myocardium, and image gathering of the fluorescence light. One example of a suitable catheter is disclosed in jointly-owned U.S. application Ser. No. 13/624,902, which is incorporated herein in its entirety. In some embodiments, the ablation technology is housed with or incorporated within the system and catheter embodiment.

Figure 3:
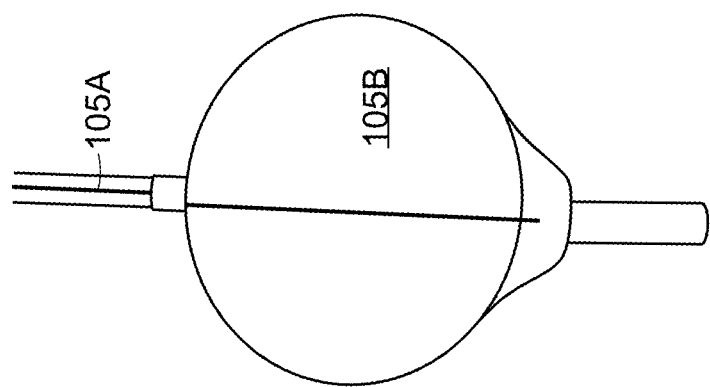
FIG. 3 is a close-up photo of an inflated catheter balloon and tip in accordance with an aspect of the present disclosure.
Figure 2:
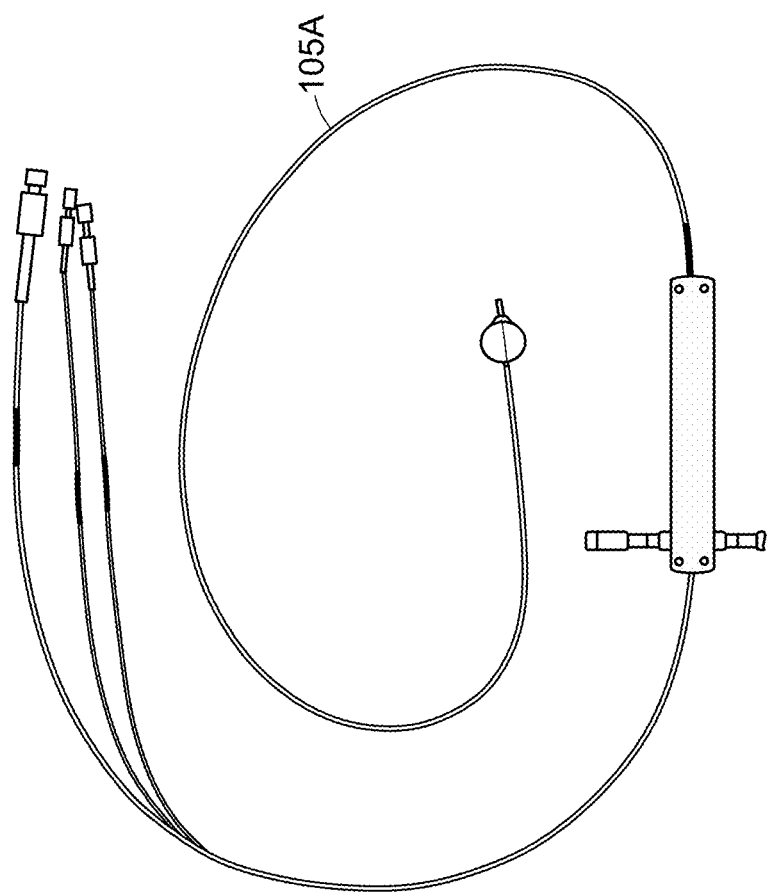
FIG. 2 is a view of a specialty catheter in accordance with an embodiment of the present disclosure.

In reference to FIG. 2 and FIG. 3, the catheter 105A may include a balloon 105B at or near the distal end of the catheter 105A. Since blood absorbs the illumination and fluorescence wavelengths, the balloon 105B may displace blood from the myocardial surface. To do so, the balloon 105B may be expandable and compliant to seat well within the anatomy—especially the pulmonary veins. The medium used to inflate the balloon 105B may also be optically transparent and yet ideally be fluoroscopically opaque for navigation purposes. Suitable inflation medium include, but are not limited to, Deuterium (heavy water) and $CO_2$, which meet both requirements. The balloon 105B may also be constructed of a material that is optically clear in at least the wavelengths of concern for both illumination of the myocardium and fluorescence. The balloon 105B may be either, made of non-compliant materials but with optimally variable sizes of best fit into pulmonary veins and other structures, or, made of a compliant material such as silicone or urethane. In some embodiments, the balloon 105B may be optically transparent in the UV range of 330 nm to 370 nm.

In some embodiments, the balloon 105B is optically clear from 330 nm to 370 nm for UV illumination and from 400 nm to 500 nm for the fluorescence wavelengths. Suitable UV-transparent materials for the balloon include, but are not limited to, silicone and urethane.

Still referring to FIG. 2 and FIG. 3, the catheter 105A may also be used to efficiently deliver the illuminating light, such as UV laser light and optionally white light, from the external light source to the balloon 105B and out of the balloon 105B to the myocardium. In some embodiments, a laser delivery fiber, usually made of quartz due to its UV efficiency and small diameter, may be used to deliver illuminating light from a UV laser light source.

The catheter of FIG. 2 and FIG. 3 may also be employed to collect and transfer the NADH fluorescence light from the illuminated tissue to an external camera (see FIG. 1A and FIG. 1B). In some embodiments, this may be accomplished via an imaging fiber bundle (see FIG. 1A) extending from the distal region of the catheter to the external camera. In some embodiments, the image bundle may include one or more of individual, single-mode fibers that together maintain image integrity while transporting it along the length of the catheter to a camera and a filter, as necessary. The imaging bundle, though flexible and small in diameter, may be able to achieve a sufficient field of view for imaging the target tissue area covered by the balloon.

The camera, can be connected to the computer system (see FIG. 1A) for viewing, and may have high quantum efficiency for wavelengths corresponding to NADH fluorescence. One such camera is an Andor iXon DV860. An optical bandpass filter of between 435 nm and 485 nm, in some embodiments, of 460 nm, may be inserted between the imaging bundle and the camera to block light outside of the NADH fluorescence emission band. In some embodiments, other optical bandpass filters may be inserted between the imaging bundle and the camera to block light outside of the NADH fluorescence emission band selected according to the peak fluorescence of the tissue being imaged.

In some embodiments, the digital image that is produced by the camera is used to do the 2D and 3D reconstruction.

In some embodiments, the image bundle may be connected to the camera, the camera may generate a digital image from NADH fluorescence (fNADH), which can be displayed on the computer. The computer processor/controller has the data of pixel intensity for pixels forming the digital image, so the computer processor/controller may use the 2D or 3D program(s) to generate the depth correlation plots. In some embodiments, the NADH fluorescence may be conveyed directly to the computer processor/controller.

Figure 4A:
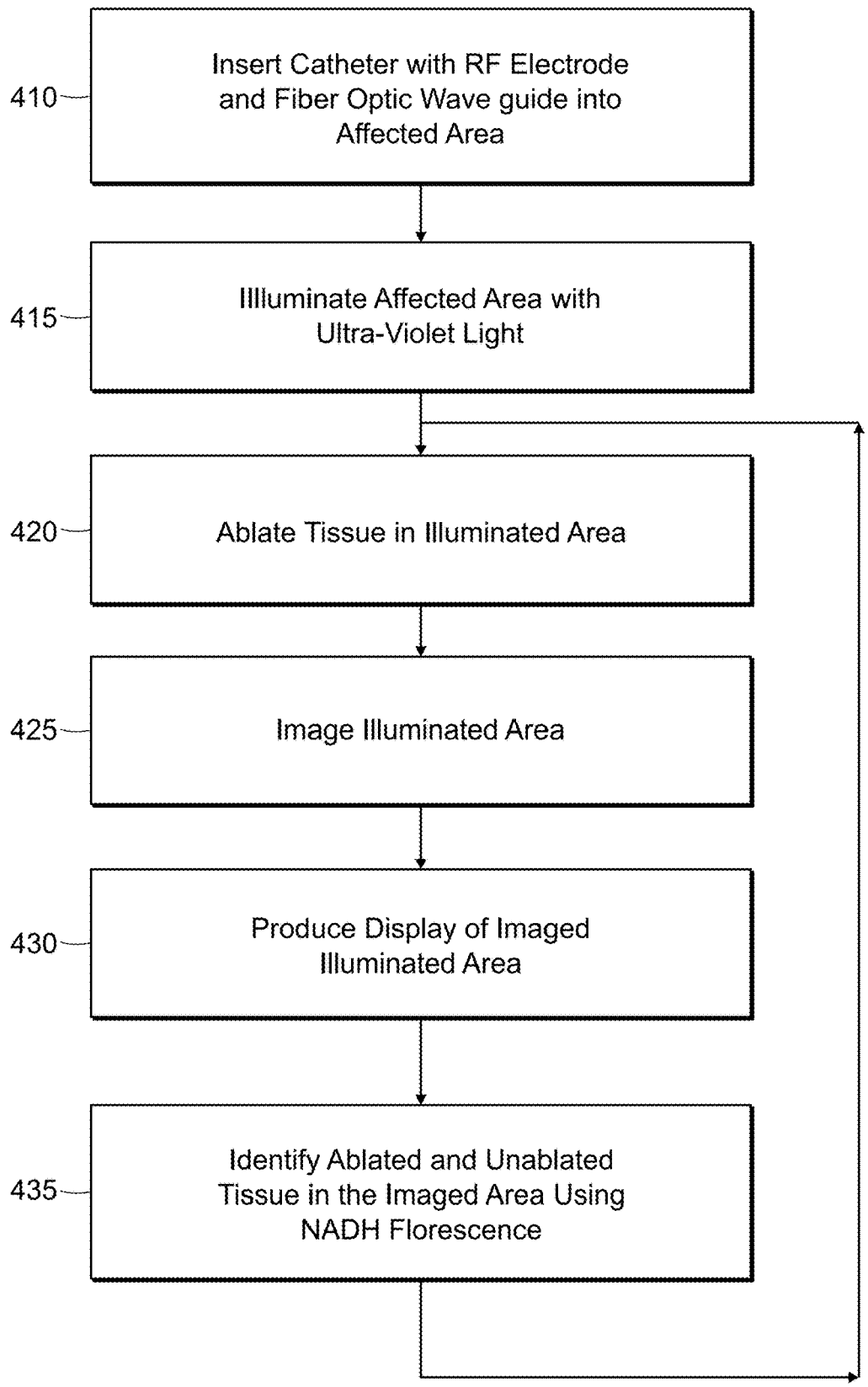
FIG. 4A is a flow diagram of a method in accordance with the present disclosure.

In reference to FIG. 4A, operation of the systems of the present disclosure is illustrated. Initially, (step 410) the catheter is inserted into the area of heart tissue affected by the atrial fibrillation, such as the pulmonary vein/left atrial junction or another area of the heart. Blood is removed from the visual filed, for example, by the balloon. For atrial fibrillation ablation a transparent balloon surrounding the fiber optic waveguide can be used to displace the blood at the pulmonary vein/left atrial junction. The affected area may be illuminated by ultra-violet light from the light source and the optical fiber or another illumination device (step 415). Tissue in the illuminated area may be ablated using an ablation device (step 420), either before or after illumination. Either point-to-point RF ablation or cryoablation or laser or other known ablation procedures may be employed using the systems of the present disclosure. Ablation proceeds by threading the tip through the central lumen of the catheter or outside the catheter. After the procedure, the ablation tip may be retracted. In some embodiments, an ablation tip may be incorporated into the catheters disclosed herein.

Still referring to FIG. 4A, the illuminated area is imaged by the combination of the imaging bundle and camera (step 425). In some embodiments, the methods of the present disclosure rely on imaging of the fluorescence emission of NADH, which is a reduced form of nicotinamide adenine dinucleotide (NAD+). NAD+ is a coenzyme that plays important roles in the aerobic metabolic redox reactions of all living cells. It acts as an oxidizing agent by accepting electrons from citric acid cycle (tricarboxylic acid cycle), which occurs in the mitochondrion. By this process, NAD+ is thus reduced to NADH. NADH and NAD+ are most abundant in the respiratory unit of the cell, the mitochondria, but are also present in the cytoplasm. NADH is an electron and proton donor in mitochondria to regulate the metabolism of the cell and to participate in many biological processes including DNA repair and transcription.

By measuring the UV-induced fluorescence of tissue, it is possible to learn about the biochemical state of the tissue. NADH fluorescence has been studied for its use in monitoring cell metabolic activities and cell death. Several studies in vitro and in vivo investigated the potential of using NADH fluorescence intensity as an intrinsic biomarker of cell death (either apoptosis or necrosis) monitoring. Once NADH is released from the mitochondria of damaged cells or converted to its oxidized form (NAD+), its fluorescence markedly declines, thus making it very useful in the differentiation of a healthy tissue from a damaged tissue. NADH can accumulate in the cell during ischemic states when oxygen is not available, increasing the fluorescent intensity. However, NADH presence disappears all together in the case of a dead cell. The following table summarizes the different states of relative intensity due to NADH fluorescence:

| Cellular State | NADH Presence | Relative Changes of Autofluorescense intensity |
| --- | --- | --- |
| Metabolically Active | Normal | Baseline |
| Metabolically Active but Impaired (Ischemia) | Increased to Hypoxia | Increased |
| Metabolically Inactive (Necrotic) | None | Full Attenuation |

Still referring to FIG. 4A, while both NAD+ and NADH absorb UV light quite readily, NADH is autofluorescent in response to UV excitation whereas NAD+ is not. NADH has a UV excitation peak of about 350-360 nm and an emission peak of about 460 nm. In some embodiments, the methods of the present disclosure may employ excitation wavelengths between about 330 to about 370 nm. With the proper instrumentation, it is thus possible to image the emission wavelengths as a real-time measure of hypoxia as well as necrotic tissue within a region of interest. Furthermore, a relative metric can be realized with a grayscale rendering proportionate to NADH fluorescence.

Under hypoxic conditions, the oxygen levels decline. The subsequent fNADH emission signal may increase in intensity indicating an excess of mitochondrial NADH. If hypoxia is left unchecked, full attenuation of the signal will ultimately occur as the affected cells along with their mitochondria die. High contrast in NADH levels may be used to identify the perimeter of terminally damaged ablated tissue.

Still referring to FIG. 4A, to initiate fluorescence imaging, the operator may deploy the balloon, which is installed around the distal portion of the catheter. Next, NADH is excited by the UV light from the light source, such as a UV laser. NADH in the tissue specimen absorbs the excitation wavelengths of light and emits longer wavelengths of light. The emission light may be collected and passed back to the camera, and a display of the imaged illuminated area may be produced on a display (step 430), which is used to identify the ablated and unablated tissue in the imaged area using NADH florescence (step 435). The process may then be repeated by returning to the ablation step, if necessary to ablate additional tissue. It should be recognized that although FIG. 4A illustrates the steps being performed sequentially; many of the steps many be performed simultaneously or nearly simultaneously, or in a different order than shown in FIG. 4A. For example, the ablation, imaging and display can occur at the same time, and the identification of the ablated and unablated tissue can occur while ablating the tissue.

The application software, executing on the computer system by the processor or computer, can provide the user with an interface to the physician. Some of the main functions can include: a laser control, a camera control, an image capture, an image conditioning (brightness and contrast adjustment, etc.), a lesion identification, a lesion depth analysis, a procedure event recording, and a file manipulation (creation, editing, deleting, etc.).

Figure 4B:
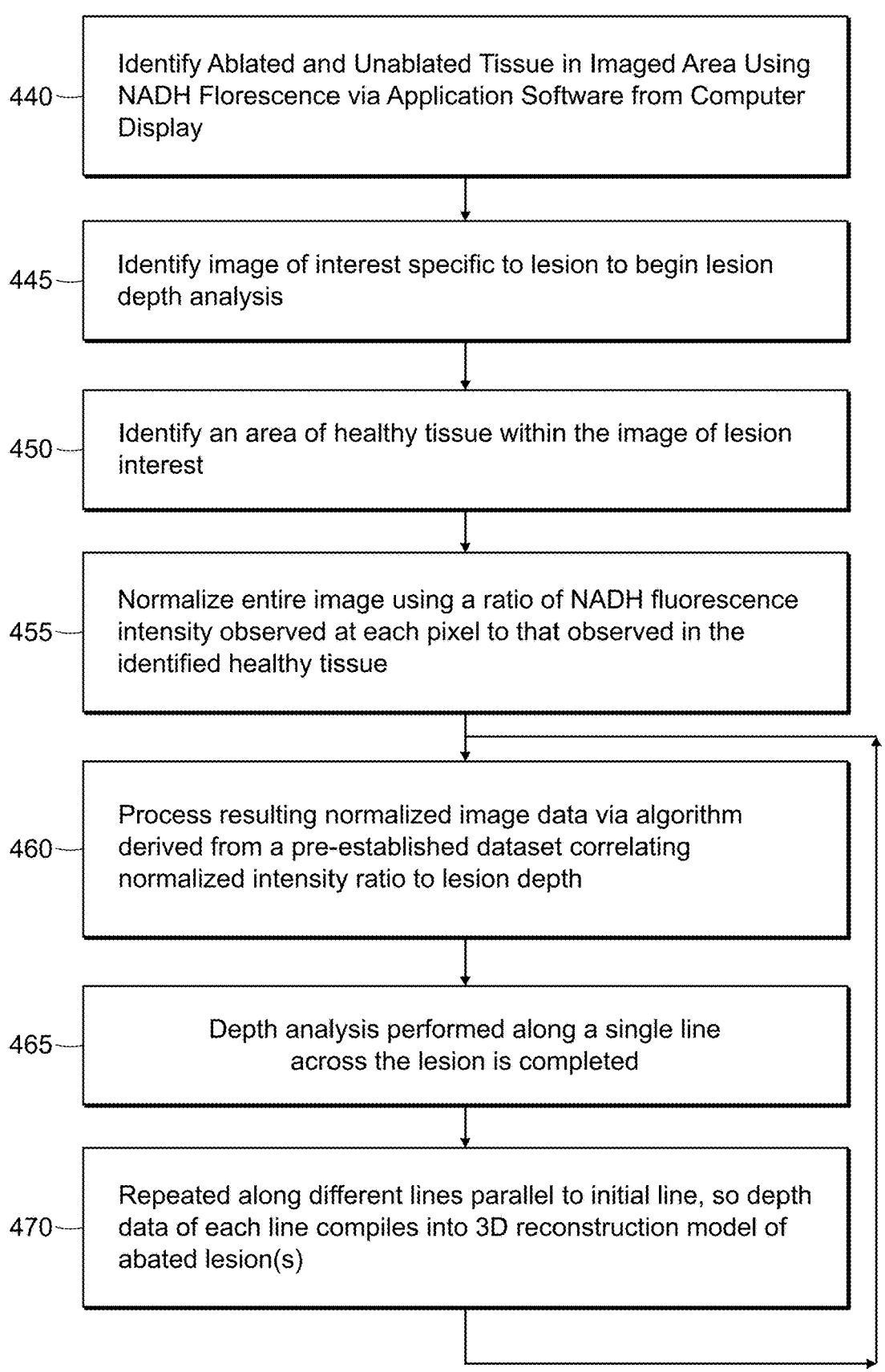
FIG. 4B is a flow diagram of a method in accordance with the present disclosure.

FIG. 4B illustrates a flow chart of the determining the lesion depth process. Step 440 discloses identifying ablated and unablated tissue in the imaged area using NADH florescence via application software from computer display. Step 445 discloses identifying an image or images of interest specific to a lesion or lesions to begin the lesion depth analysis. Step 450 discloses identifying an area of healthy tissue within the image of lesion of interest. By way of a non-limiting example, referring to FIG. 6A and FIG. 6B, imaging fluorescence of NADH in the heart can produce a display of the physiology of the lesion site having a dark appearance due to lack of fluorescence, gaps having light appearance due to normal fluorescence, and any ischemic tissue having a brighter halo type appearance surrounding the lesion site (see FIG. 6A and FIG. 6B). Once the lesion or lesions are identified, they are selected for lesion depth analysis.

Step 455 discloses normalizing the entire image using a ratio of NADH fluorescence intensity observed at each pixel to that observed in the identified healthy tissue. Step 460 discloses processing the resulting normalized image data via an algorithm derived from a pre-established dataset correlating normalized intensity ratio to lesion depth. Lesion depth can be computed using the ratio of healthy tissue fluorescence to lesion tissue fluorescence. First, the user identifies an area of healthy tissue within an image. The application software then normalizes the entire image using the ratio of NADH fluorescence intensity observed at each pixel to that observed in the identified healthy tissue. The resulting normalized image data is then processed via an algorithm derived from a pre-established dataset correlating normalized intensity ratio to lesion depth. By using the patient's own myocardial NADH fluorescence as a control, this method drastically reduces the impact of patient-to-patient variations in absolute NADH fluorescence, as well as optical losses in the illumination and imaging systems and optical intensity variations resulting from specular and diffuse reflections, and other optical non-idealities.

Step 465 discloses the depth analysis performed along a single line across the lesion is completed. It is also possible that this can be done for just one single location in the lesions from information from a single location, a line or a region. FIGS. 4C-4F show the depth analysis performed along a single line. For example, FIG. 4C shows an image a canine heart that has been ablated six times. The square encases a single ablation lesion. FIG. 4D shows in the top right is an NADH fluorescence (fNADH) image obtained from the same area of a blood perfused canine heart. FIG. 4E is a 2d depth map performed along a single line and generated based on the digital image in FIG. 4D, that is, from the intensity of pixels forming the digital image. FIG. 4F is a hematoxylin and eosin stained canine heart tissue cut along the same line, which illustrates the actual depth of the lesion (the square illustrates the border of the lesion), with the deepest area corresponding to the darkest spot in FIG. 4D and the lowest fNADH in FIG. 4E.

Step 470 discloses repeating steps 460 to 470 along different lines parallel to the initial line, so the depth data of each line compiles into a 3D reconstruction model of the lesion site(s). The depth analysis process performed along a single line across the lesion could be repeated as many times as needed along different lines parallel to the initial line, and the depth data of each line could be compiled into a 3D reconstruction model of the lesion site.

Figure 4H:
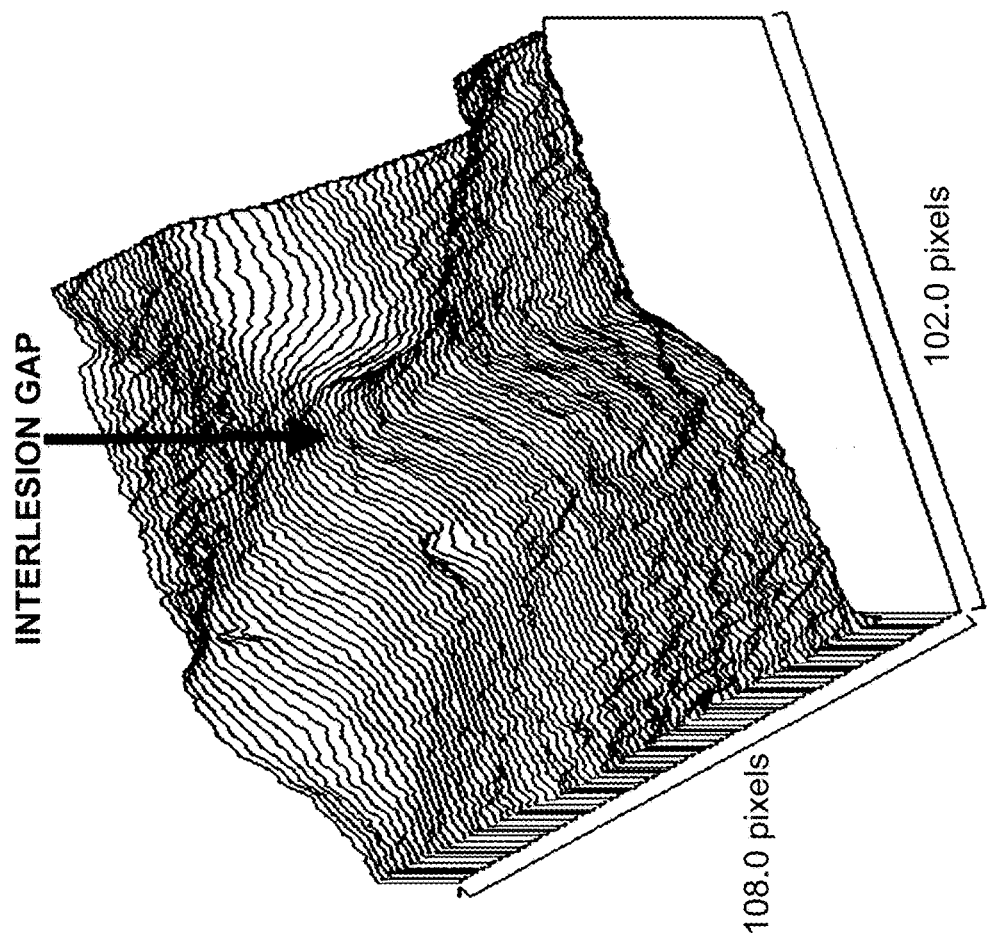
FIG. 4G and FIG. 4H shows the depth analysis in 3D with two ablation lesions and inter-lesion gap imaged with by fNADH, in accordance with the present disclosure.
Figure 4G:
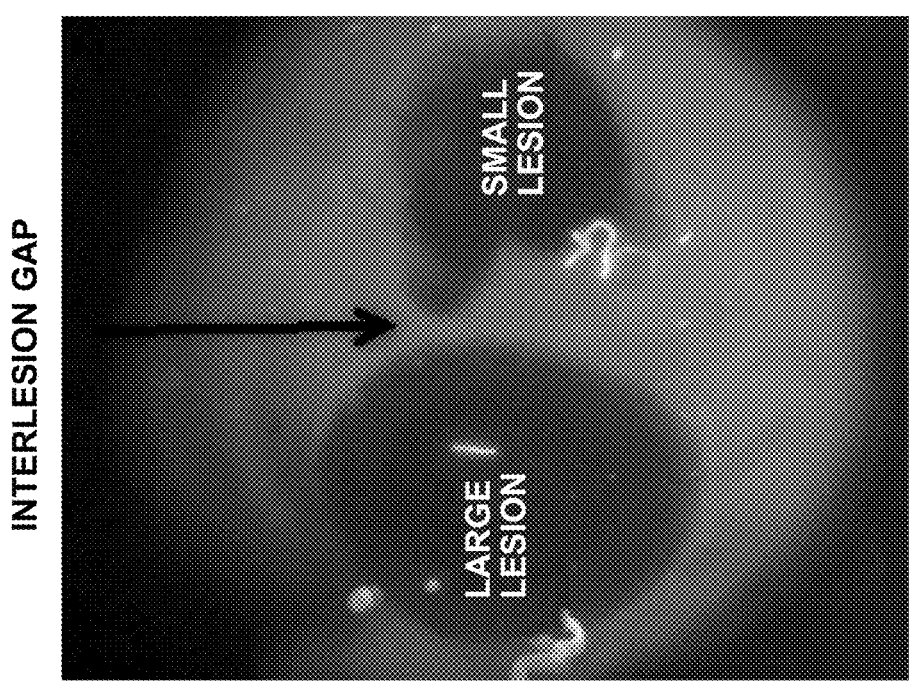

By way of a non-limiting example, FIG. 4G shows a digital image of two ablation lesions and inter-lesion gap imaged with by fNADH. FIG. 4H shows a 3D reconstruction from pixel intensity in the digital image of FIG. 4G. Both the 2D data and the 3D data may be used for further diagnosis or treatment, as described above.

The intensity of fluorescence detected by the camera can be measured and plotted with the lowest fluorescence (darkest) corresponding to the deepest lesions and the highest fluorescence (lightest) corresponding to the unablated or healthy tissue. Any levels of gray between the extremes of light and dark generally correspond to the degree of tissue lesion depth. The sensitivity of the camera sensor determines the number of levels of gray between completely black and completely white. A few binary numbers are common in such applications including 256-level and 65,536-level, corresponding to 8-bit and 16-bit resolution, respectively. In the case of 8-bit sensitivity, 0 would be completely black and 255 completely white, with 254 levels of gray in between. Using this gray-scale image, a suitable depth map can be estimated. In some embodiments, 24 bit resolution may also be used.

It is noted that fNADH imaging can reliably and reproducibly predict cardiac ablation lesion diameter and depth. The loss of fNADH intensity correlated with actual measured diameter and depth of multiple RF lesions with a correlation coefficient of greater 96% and 79%, respectively. It is possible that the loss of correlation at lesion depths greater than 2 mm occurred due to the inability of UV illumination to reliably penetrate cardiac tissue below this depth. With further lesion depth, no further fNADH could be detected and a reproducible plateau in fNADH signal intensity was thus observed at lesion depths of about 2 mm. The mean left atrial wall thickness at locations in the left atrium that are often targeted for ablation is 1.85 mm as measured by CT scans. Therefore, the observed nadir and plateau of fNADH signal intensity across an RF lesion serves as a plausible model for a clear, all-or-none determination of sufficient lesion depth.

The methods, systems and devices disclosed herein can be used for a variety of therapeutic procedures. Exemplary procedures in which the methods, systems and devices disclosed herein can be utilized include, but not limited to, for diagnostic and therapeutic procedures in the heart, for treating arrhythmias, such as, for example, supraventricular arrhythmias and ventricular arrhythmias, for treating atrial fibrillation, and pulmonary vein mapping and ablation. The ablated tissue may be cardiac muscle (epicardial or endocardial heart muscle), but the methods disclosed herein should have the same effect on skeletal muscle, liver, kidney, and other tissues with significant presence of NADH-rich mitochondria.

The presently disclosed methods can be used with two dimensional (2D) to three dimensional (3D) mapping protocols. A plurality of 2D images can be superimposed onto a 3D reconstruction image of the tissue or organs, including the heart. Many arrhythmia procedures include the use of reconstructed three dimension images of the patient's specific anatomy during the procedure. Using a variety of imaging modalities including computed tomography (CT), magnetic resonance imaging (MRI), ultrasound, and electroanatomical mapping using systems such as NAVX and CARTO. In all cases, the three dimensional anatomical images or surfaces present patient specific anatomy to help target areas of tissue to treat. In all cases, the ability to visualize the precise location where lesions are formed and the precise locations where lesions are missing, e.g., the "gaps" or breaks in the lesion set, would guide the procedure to optimize the therapeutic outcome. 2D image to 3D image mapping allows the system to superimpose, spatially register, and/or texture map single or multiple images of tissue (that may indicate presence or absence of lesions) with the specific anatomy of the patient in a three dimensional, rotatable, interactive virtual environment.

In some embodiments, the systems and methods of the present disclosure allow the registration and/or overlay of the images produced by the system onto the specific anatomy of the patient as seen using other imaging modalities such as an MRI image, computed tomography (CT) image, ultrasound image and three dimensional reconstructions thereof. In some embodiments, the systems and methods of the present disclosure may further include the registration and/or overlay of the images produced by the system onto the specific anatomy of the patient as seen using other electroanatomical mapping, anatomical reconstruction, and navigational systems such as NAVX and CARTO. The registration and overlay may be performed during the procedure in real time. Texture mapping NADH images onto reconstructed endocardial surfaces permits visualization of the treatment site. For example, multiple NADH snapshots of lesions could create a full panoramic image of the entire pulmonary vein opening, or multiple pulmonary veins. Positioning sensors on the catheter tip could provide information that will allow the NADH images to be combined together to create a 3D reconstruction image.

Examples of using the systems and methods of the present disclosure are provided below. These examples are merely representative and should not be used to limit the scope of the present disclosure. A large variety of alternative designs exists for the methods and devices disclosed herein. The selected examples are therefore used mostly to demonstrate the principles of the devices and methods disclosed herein.

EXAMPLES

Experiments were conducted with a functionally equivalent system to produce ablated lesions and lesion images in order to develop methods of lesion depth analysis. The experiment set is described below.

NADH Fluorescence System provided that the epicardial surface was illuminated using an LED spotlight with a peak wavelength of 365 nm (PLS-0365-030-07-S, Mightex Systems). Emitted light was bandpass filtered at 460 nm+/−25 nm and imaged using a CCD camera (Andor Ixon DV860) fitted with a low magnification lens. The fluorescence of NADH (fNADH) was imaged to monitor the state of epicardial tissue.

The RFA System provided that RFA was performed with a standard clinical RF generator (EPT 1000 ablation system by Boston Scientific). The generator was electrically interfaced to the animal via a 4 mm cooled Blazer ablation catheter (Boston Scientific) in order to deliver lesions. A grounding pad was used at the time of ablation. The generator was set to temperature control mode. Cryoablation were performed using custom-made metal probe dipped in liquid nitrogen or by using Freezor MAX Cardiac CryoAblation Catheter by Medtronic.

Referring to FIG. 5A and FIG. 5B, first, baseline data were obtained for the NADH excitation and emission spectrum in healthy cardiac tissue. FIG. 5A and FIG. 5B show the tissue excitation-emission matrices. Due to the presence of NADH, healthy tissue emits strongly between 450 nm and 470 nm when excited in the range of 330 nm to 370 nm. The large peak associated with NADH is absent in ablated tissue.

An example of a typical RFA lesion is shown in FIG. 6A and FIG. 6B. The image on the left is captured using white light illumination while the f NADH image on the right is captured using UV excitation with a 460 nm filter.

All animal protocols were reviewed and approved by the Animal Care and Use Committee at George Washington University School of Medicine and conformed to the guidelines on animal research.

Ex vivo experiments were initially conducted using excised, blood-free hearts of a rat (200-300 g Sprague-Dawley). The animals were heparinized and anesthetized using standard procedures. The chest was opened using a midline incision. Hearts were then excised; the aorta was cannulated and Langendorff-perfused at constant pressure. The hearts were placed on top of a grounding pad and submerged in 37 degree Celsius Tyrode solution during RFA ablation. Alternatively cryoprobe was applied directly to the epicardial surface.

Radiofrequency energy was applied to the epicardium of excised, blood-free rat ventricles while varying temperature and duration to generate RFA lesions of different sizes. A uniform contact force of 2 grams as measured by a calibrated balance. Lesions of different sizes were generated by varying the temperature (50, 60 and 70 Celsius) and time (10, 20, 30, 40, 50 seconds) of RF applications. A total of twelve RFA lesions were generated on six different rat heart specimens.

NADH fluorescence of lesions and surrounding tissue was measured by illuminating the epicardial surface with UV light at 365 nm using a Mightex Precision LED spotlight. Light corresponding to fNADH was selected using a 460/25 nm bandpass filter and imaged using a high-sensitivity charge-coupled device camera. Lesions were additionally imaged with bright light adjacent to a tape measure to allow for measurement of the size of lesions. fNADH images were then imported into ImageJ software to measure the size and analyse the darkness profile of each lesion. Darkness profile was assessed by placing a linear region of interest (ROI) through the center of each fNADH imaged ablation lesion to measure pixel intensity at each point across the lesion periphery. Ventricular tissue was then retrograde-perfused with Tyrode solution containing Triphenyltetrazolium chloride (TTC) to assess for tissue necrosis. Epicardial lesions were excised for gross and histologic measurement of tissue injury.

In vivo experiments were conducted using canine open-chest models. The animals underwent open-chest surgery after induction of general anesthesia. Using a 4 mm radiofrequency ablation catheter, multiple lesions were given to the epicardial surface at various durations and temperatures. The epicardial surface of the heart was then illuminated with a UV light at 365 nm (Mightex precision LED spot light) and the corresponding fNADH was passed via a 460/25 nm filter coupled to a high quantum efficient fluorescence camera (Andor Ixon DV860 camera). The lesions were imaged under bright white light with a tape to measure the size of the lesions.

Postmortem Examination provided that after the rat experiments, the animal hearts were stained with TTC. TTC is a standard procedure for assessing acute nectosis, which relies on the ability of dehydrogenase enzymes and NADH to react with tetrazolium salts to form a formazan pigment. Metabolically active tissue appeared crimson while necrotic tissue appeared white. After TTC staining, the lesions were bisected at the central linear ROI as defined prior for pixel intensity analysis for the measurement of lesion depth across the corresponding ROI. Lesion morphology, width, length and depth were determined and recorded at gross examination.

For the canine experiment, sections of multiple epicardial lesions were bisected longitudinally and submitted for histological staining (hematoxylin-eosin). Specimens were then analyzed under light microscopy at 40× to characterize the morphological changes for determination of the degree of heat-induced cell damage and necrosis.

The statistical analysis included that two independent readers measured lesion size by fNADH and TTC stain with means and standard deviations recorded. Correlation coefficients of lesion size by fNADH and by TTC stain were also obtained and recorded.

Figure 7A:
FIG. 7A is a photo of an epicardial image showing a diameter measurement of a lesion viewed under UV illumination.
Figure 7B:
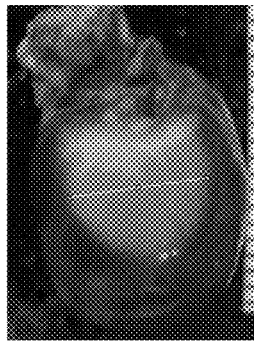
FIG. 7B is a photo of a diameter measurement of the same lesion in FIG. 7A, but as stained by triphenyltetrazoliun chlorate (TTC).
Figure 7C:
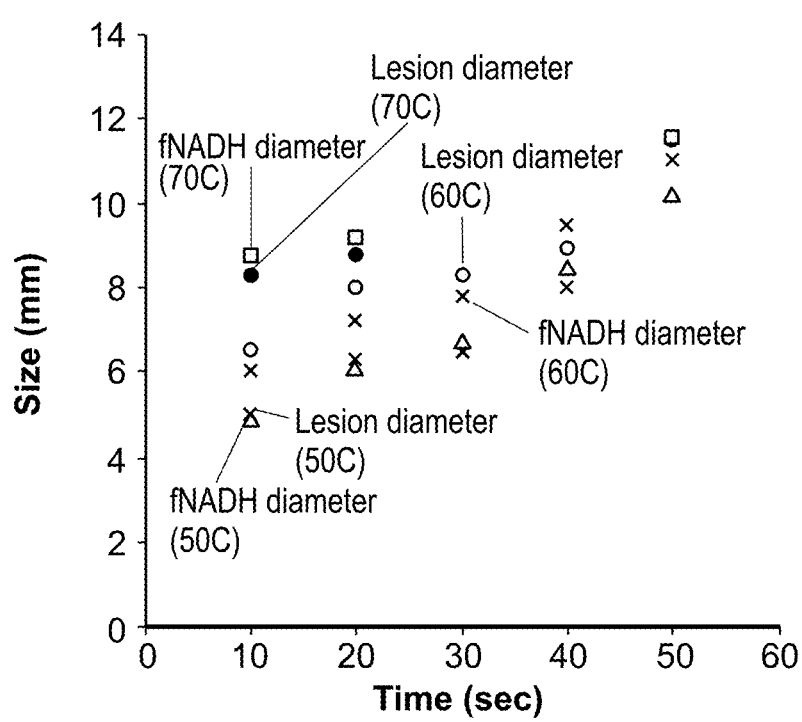
FIG. 7C is a plot of the correlation of a lesion size diameter measurement of the fluoresced lesions and TTC stained lesions.

The results includes that the Epicardial fNADH was first correlated to lesion size. In the rat model, a total of 12 epicardial surface lesions were delivered and measured by two independent readers using fNADH and triphenyltetrazolium chloride (TTC) stain (see FIG. 7A, FIG. 7B, and FIG. 7C). A typical fNADH image is illustrated in FIG. 7A, and the actual lesion diameter measurement using TTC stain is shown in FIG. 7B. Linear measure of lesion diameter using TTC (top image, 7A) correlated with lesion diameter obtained from the corresponding fNADH image (bottom image, 7B). FIG. 7C shows a summary graph of lesion size vs. ablation delivery times. For all lesion sizes, epicardial fNADH closely predicted the actual lesion diameter as determined by TTC staining Average NADH and TTC diameter was 7.9±1.85 mm and 8.2±1.95 mm, respectively with a correlation coefficient of 96%.

Figure 8A:
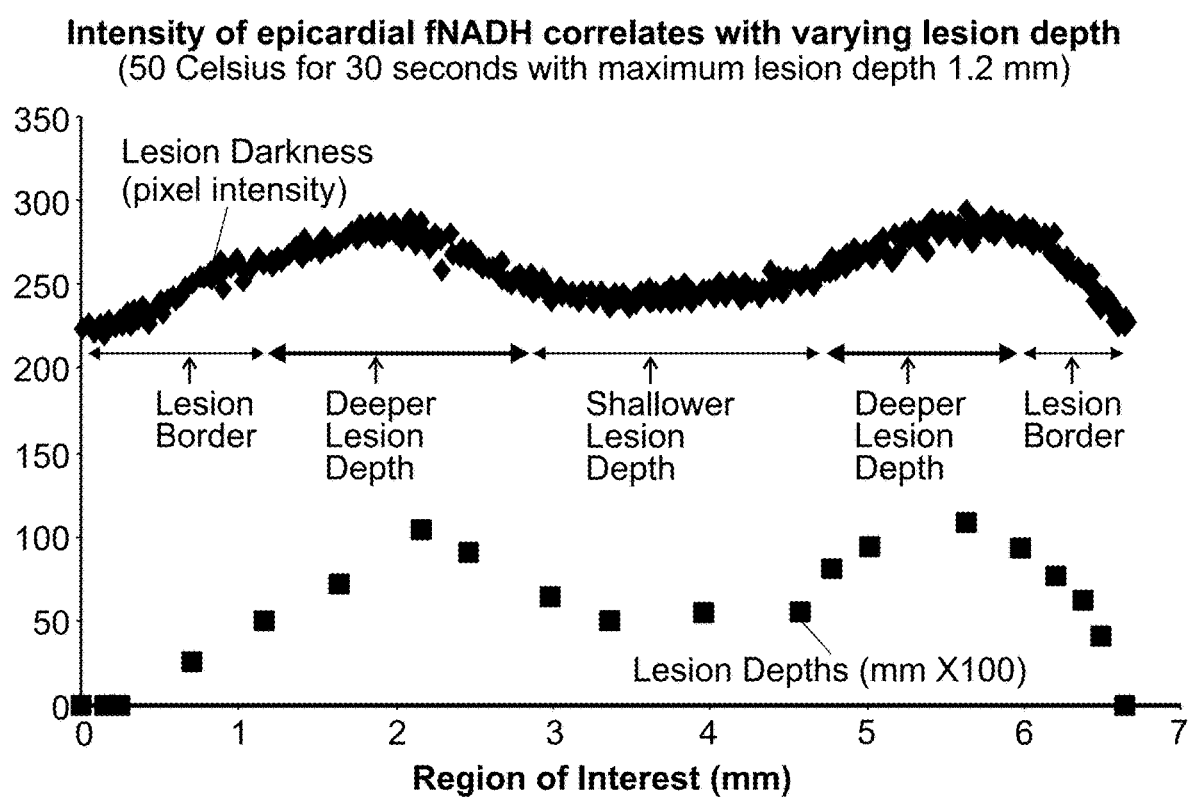
FIG. 8A is a plot of a correlation of a lesion depth to NADH fluorescence.
Figure 8B:
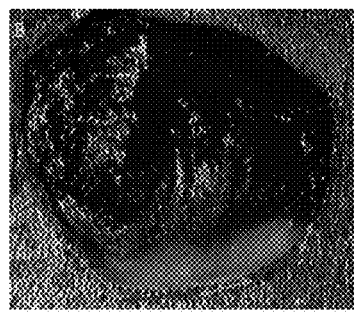
FIG. 8B is a photo of a diameter measurement of two lesions revealed by staining with TTC.
Figure 8C:
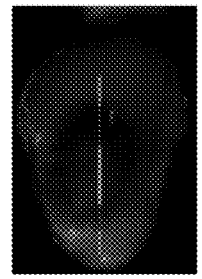
FIG. 8C is a photo of a diameter measurement of fNAHD visualized lesions.
Figure 8D:
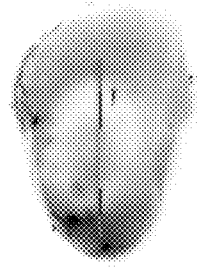
FIG. 8D is an inverted signal of FIG. 8C.

Temperature and lesion delivery times were varied to obtain a multitude of epicardial surface lesions at varying depths in rat hearts. The intensity of epicardial fNADH was then measured multiple times along the centerline of the lesions. An example lesion set is shown on FIG. 8A, FIG. 8B, FIG. 8C, and FIG. 8D with the fNADH graphed in the top panel (FIG. 8A) for the line across lesion #1 in FIG. 8C. FIG. 8B shows the measured depth obtained from the TTC stained heart across the same lesion. FIG. 8D shows the inverted image of fNADH used in the graph (FIG. 8A). This was done so that higher intensities of inverted fNADH would correlate with the depth of lesions shown and have a similar shape.

Figure 9:
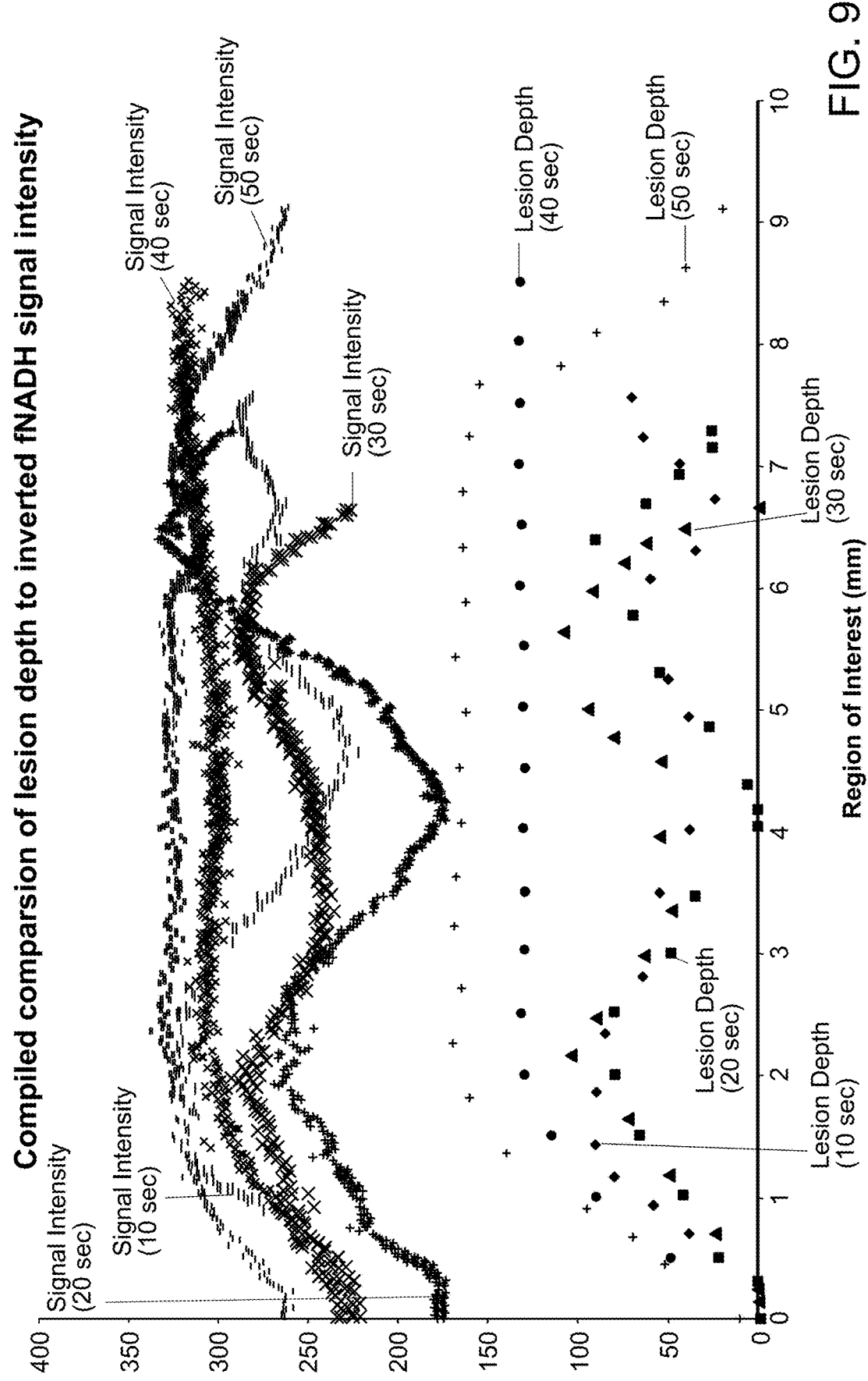
FIG. 9 is a plot of compiled data comparing a lesion depth to inverted NADH fluorescence intensity.
Figure 10:
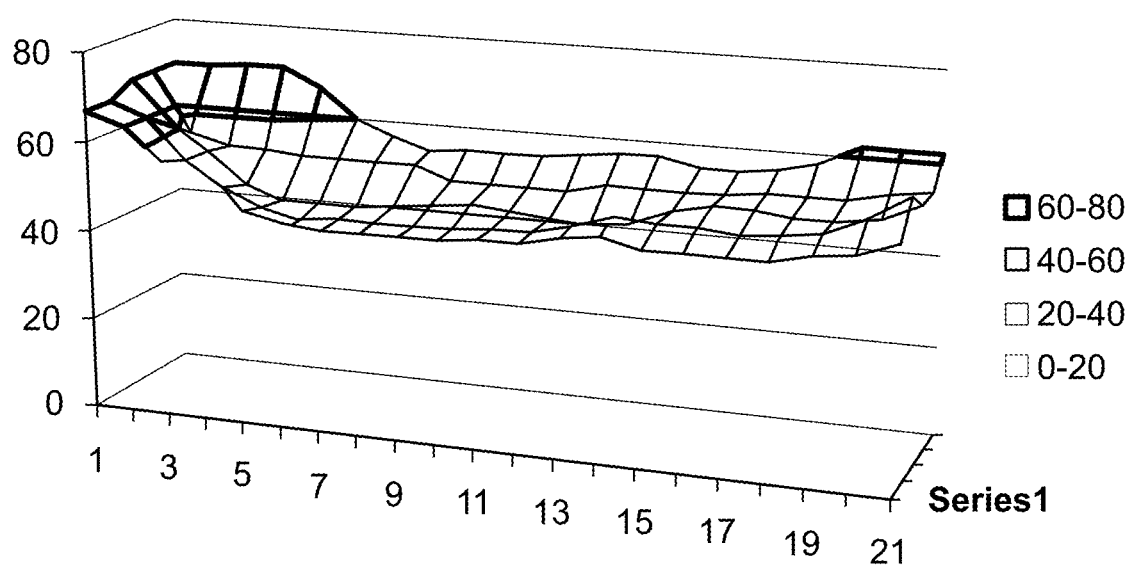
FIG. 10 is a 3D reconstruction of a depth of a lesion.

Referring to FIG. 9 and FIG. 10, the lesion depth was compared to the inverted fNADH signal intensity that was compiled and ploted in FIG. 9. Additionally, lesions were delivered for 10, 20, 30, 40 and 50 seconds respectively at 50 degrees Celsius. The same comparisons were obtained at varying temperatures and showed similar findings (see FIG. 9 and FIG. 10).

Figure 11:
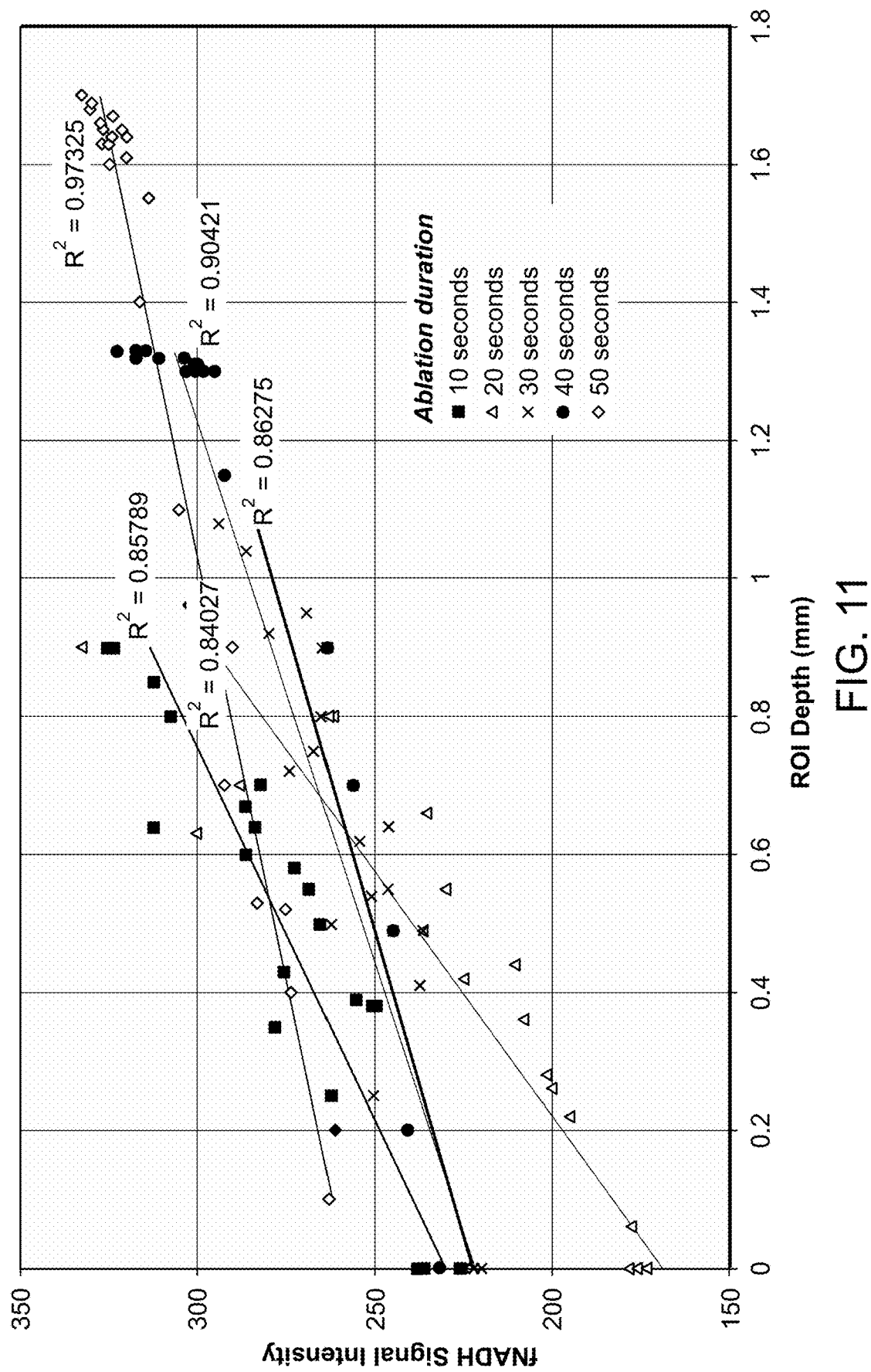
FIG. 11 is a plot of NADH fluorescence intensity versus a lesion depth varying ablation duration (time).
Figure 12B:
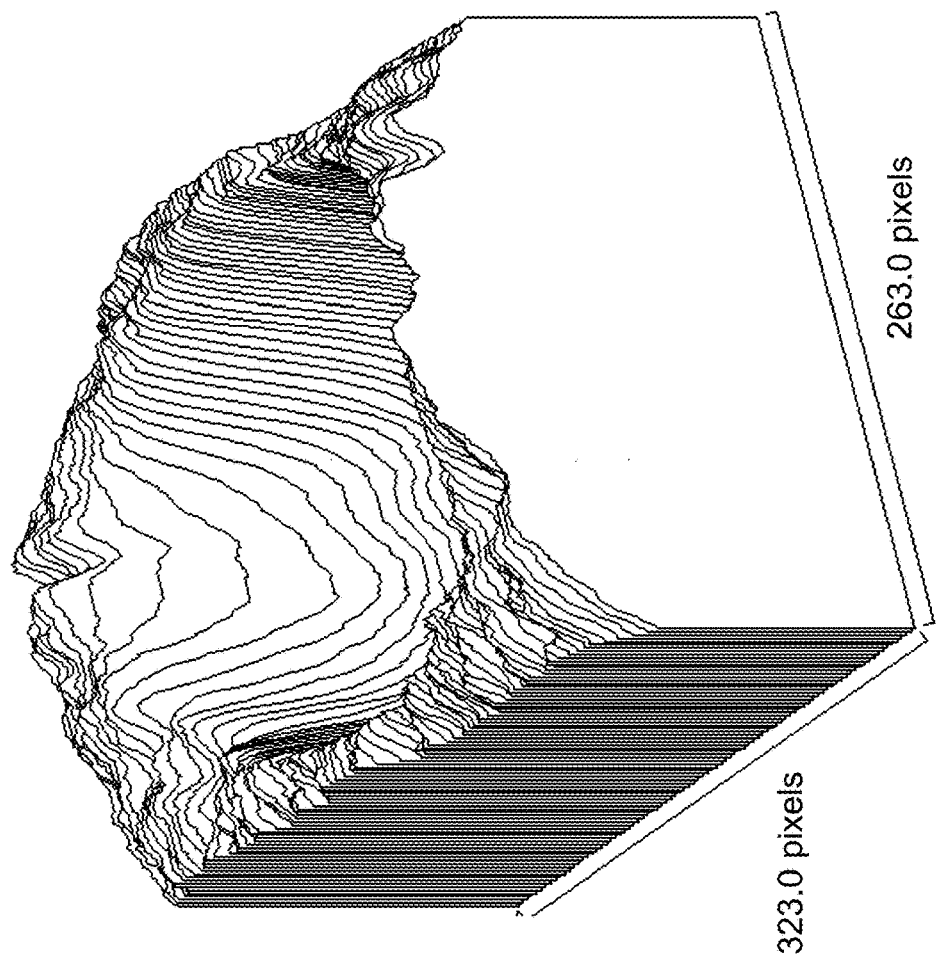
FIG. 12A and FIG. 12B illustrate a lesion formed by cryo ablation and a 3D plot of the lesion, respectively.
Figure 12A:
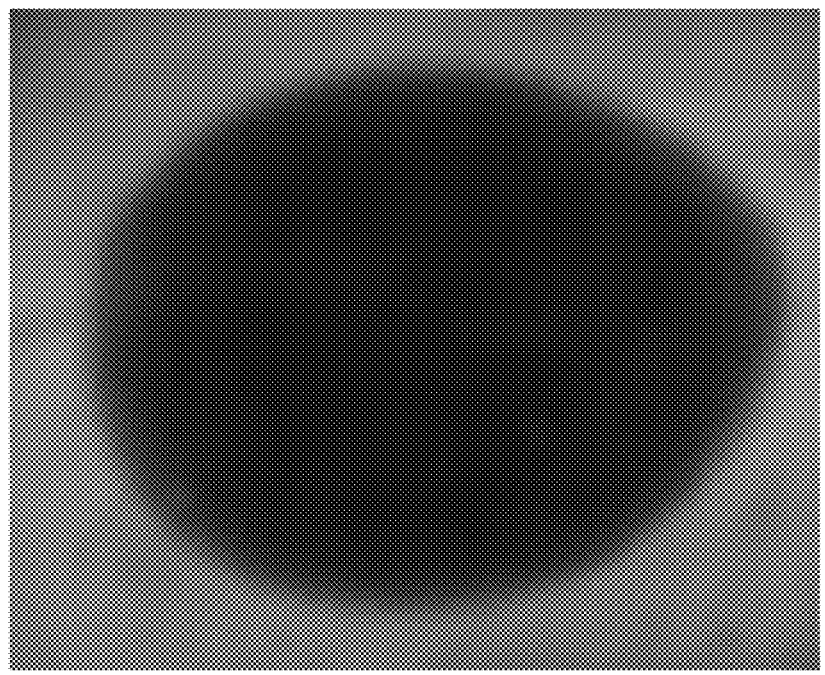
Figure 12D:
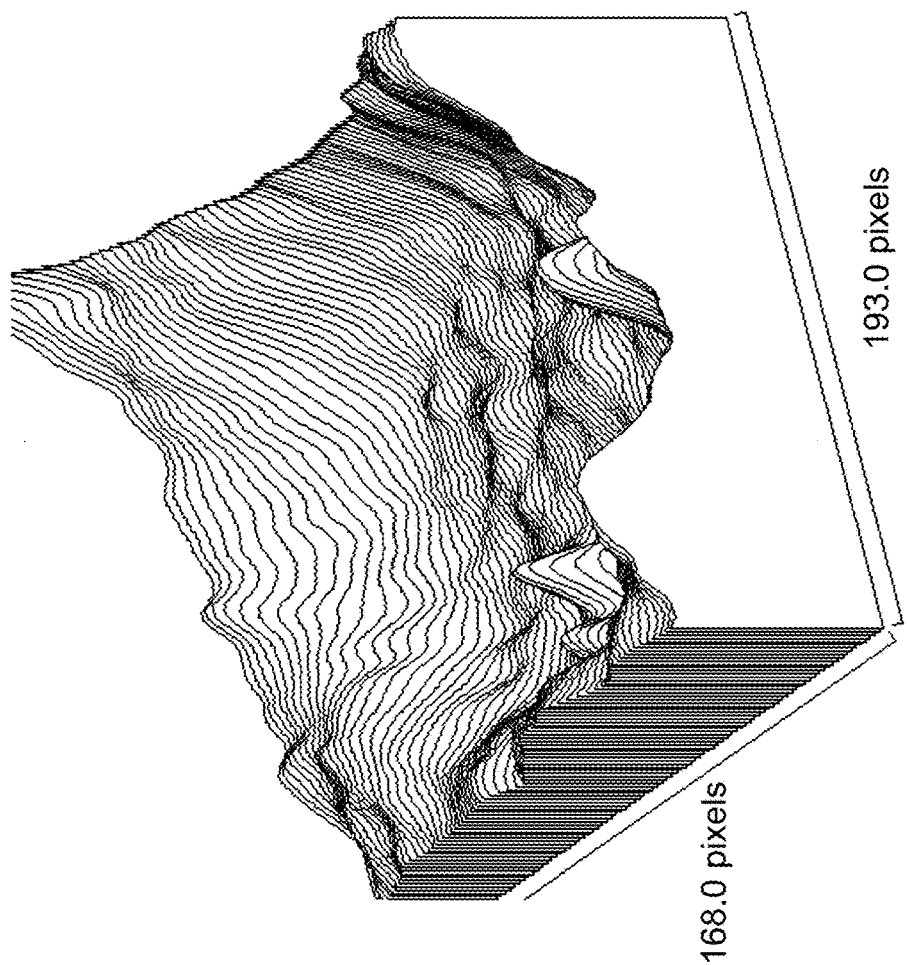
FIG. 12C and FIG. 12D illustrate a lesion formed by radiofrequency ablation and a 3D plot of the lesion, respectively.
Figure 12C:
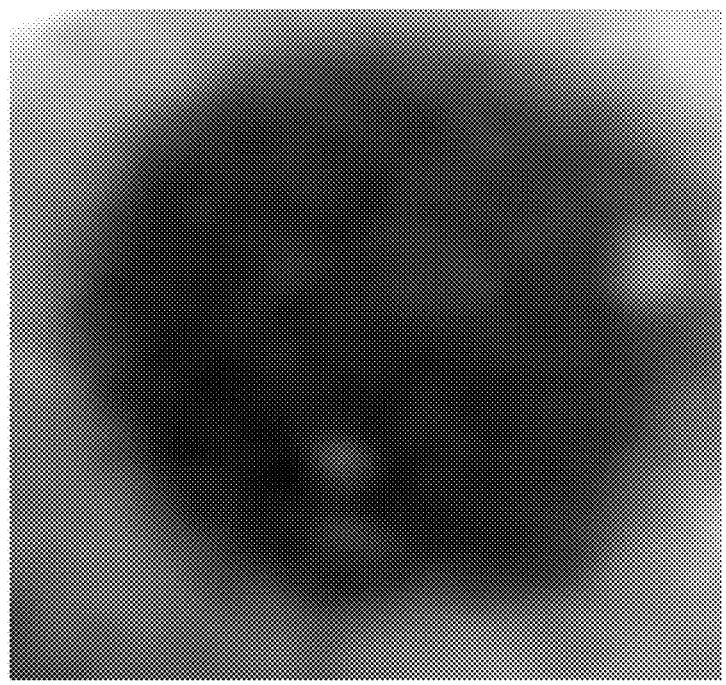
Figure 12F:
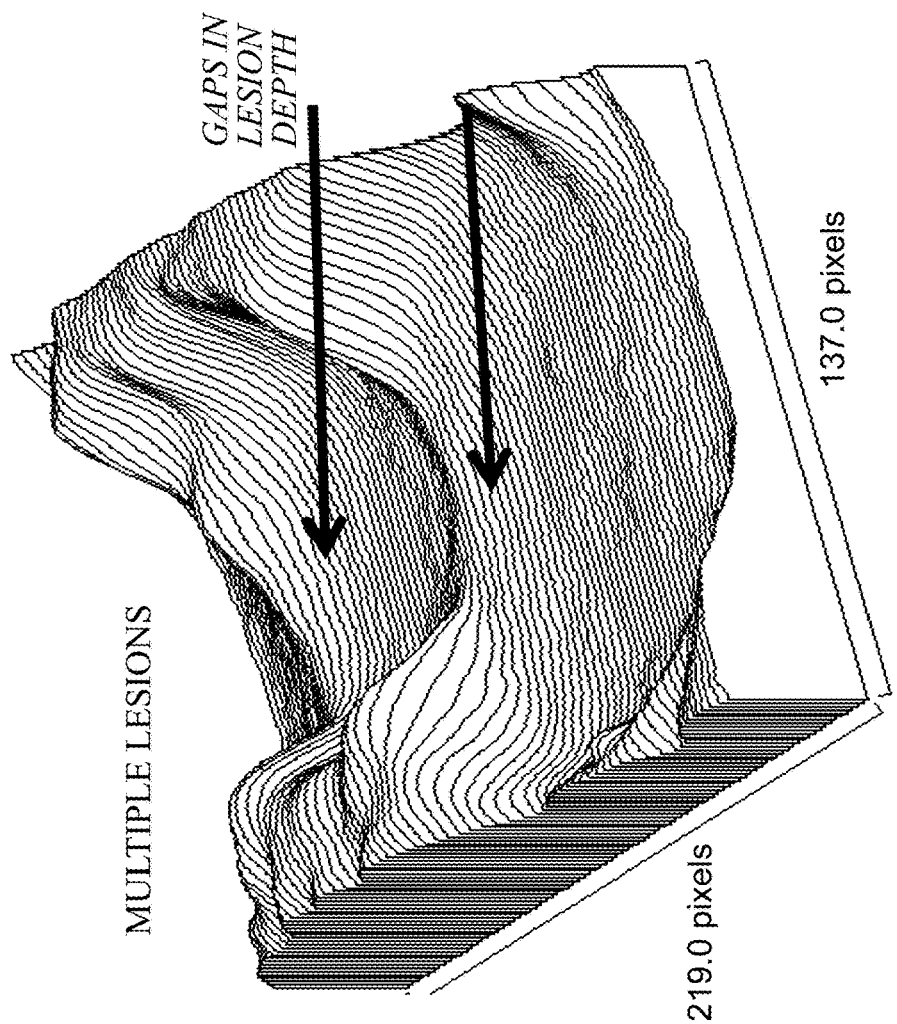
FIG. 12E and FIG. 12F illustrate three different lesions and a 3D plot showing a physical relation of the corresponding depths of the lesions, respectively. Interlesion gap is illustrated on the 3-D reconstruction image.
Figure 12E:
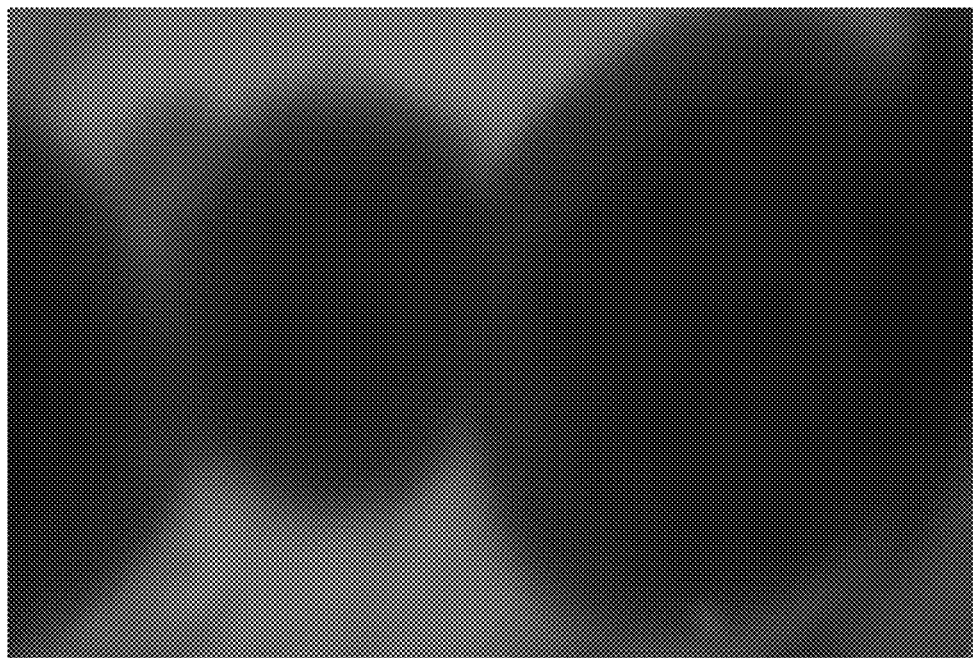

Referring to FIG. 11, a linear correlation coefficient was obtained for different duration times at a specified temperature using lesions made by varying temperature and lesion duration. FIG. 11 shows the results at 60 degrees Celsius with correlation coefficients ranging from 0.84 to 0.97 depending on the duration of ablation.

3D reconstruction of lesion depth was obtained from canine epicardial images by gathering gray scale from individual maps of fNADH using only 5 parallel lines across the lesion and plotting values using a 3D graphing program.

FIG. 12A and FIG. 12B, FIG. 12C and FIG. 12D, and FIG. 12E and FIG. 12F show higher resolution 3D reconstructions of a cryolesion, a radiofrequency lesion, and multiple cryolesions, respectively. Of note are the variations in lesion depth visible in the plot displaying multiple lesions.

The experimental results validate fNADH as an accurate measure of epicardial lesion size and as a predictor of lesion depth. 3D reconstruction of depth is possible by repeating the methods described above along multiple lines through the ablation image and compiling the results (see FIG. 10, FIG. 12A, FIG. 12B, and FIG. 12C).

Figure 13A:
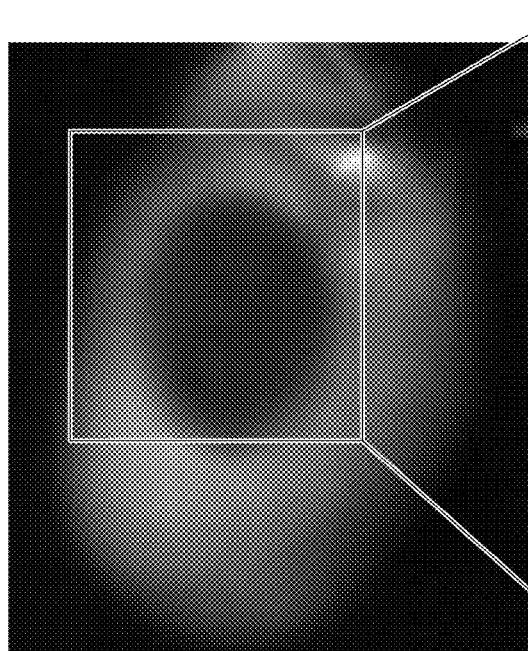
FIG. 13A is an image of a lesion formed by cryprobe.
Figure 13B:
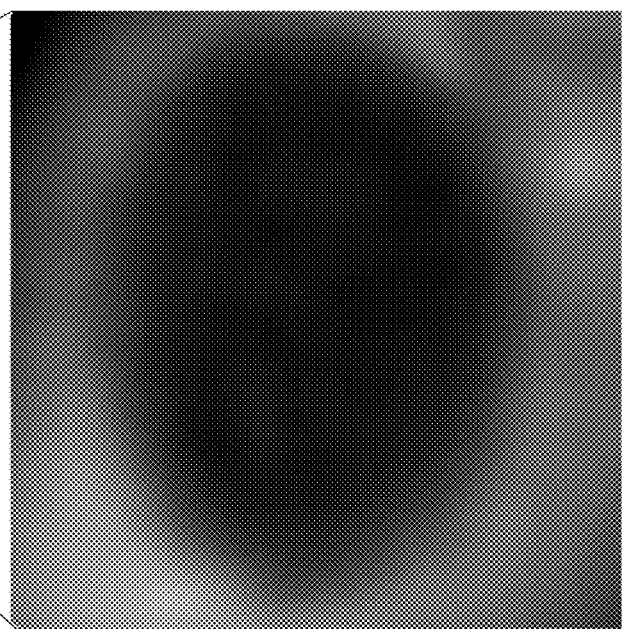
FIG. 13B is an enlargement of the lesion of FIG. 13A.
Figure 13C:
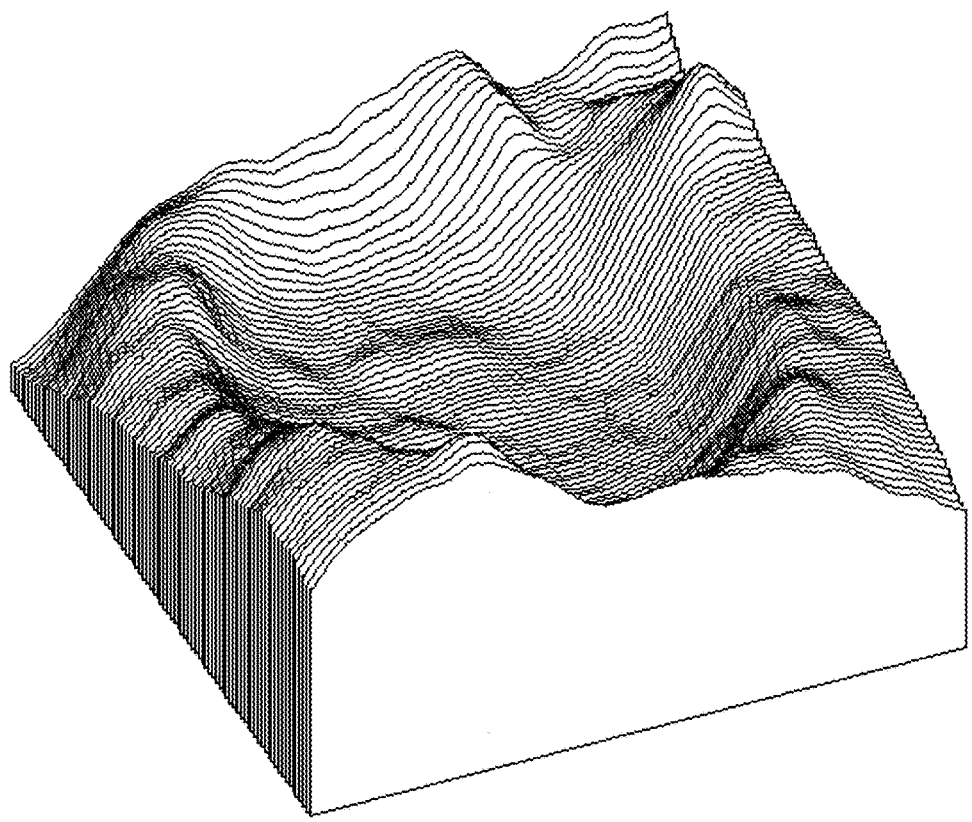
FIG. 13C is a 3D plot of the lesion formed by cryprobe of FIG. 13A.

FIG. 13A shows an fNADH image of an ablated lesion created by using a cryo ablation catheter, for example, and FIG. 13B is a magnified image of the same, as noted above. FIG. 13C shows the 3D depth reconstruction correlation plot of that same ablated lesion. The main difference is that FIG. 12 includes some ablation lesions created with RFA, wherein RFA and cryo lesions have a different appearance in 3D.

Figure 14:
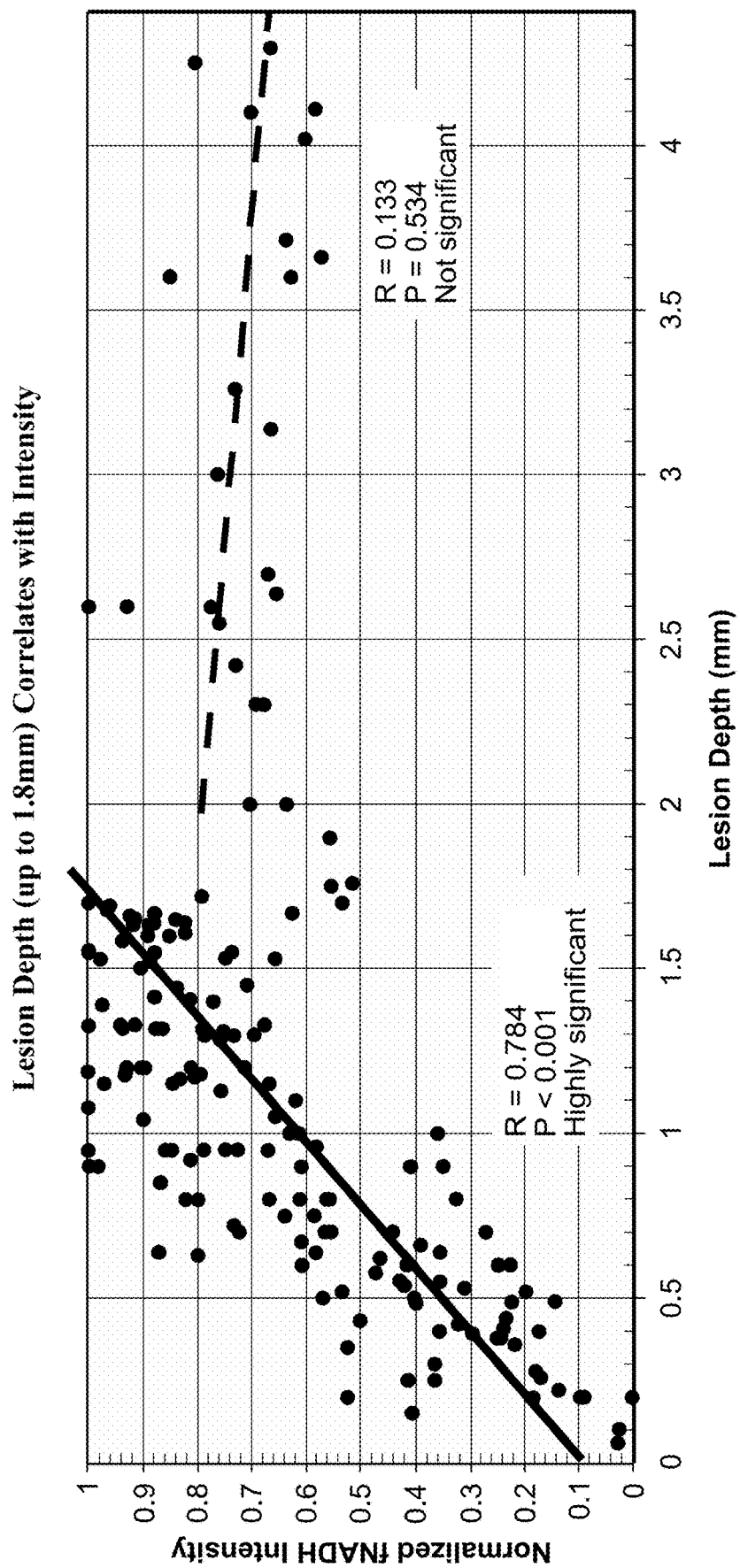
FIG. 14 shows a plot of an intensity of epicardial fNADH correlated in an inverse manner with an actual lesion depth as measured by TTC analysis.

Referring to FIG. 14, the RFA lesions were detectable and distinguishable from viable tissue with excellent resolution since they exhibited very low or non-detectable fNADH as compared to the surrounding, healthier myocardium. Lesion diameter, as imaged by fNADH, closely correlated to measured lesion size by TTC (average NADH and TTC diameter 7.9±1.85 mm and 8.2±1.95 mm, respectively; correlation coefficient [CC] 96%). The intensity of epicardial fNADH correlated in an inverse manner with actual lesion depth as measured by TTC analysis. This relationship was reproduced with a CC of over 79% for all RFA variables up to a lesion depth of 1.8 mm (significance $p<0.0001$) beyond which the fNADH signal intensity became saturated and plateaued, as shown in FIG. 14.

Relationship of lesion depth to epicardial fNADH was reproducible with statistical significance. Multiple lesions of different size were generated on the epicardium of rat ventricles by varying RF duration and temperature. Analysis of lesion depth to inverse fNADH signal intensity was performed on these multiple lesions. Loss of fNADH intensity correlated with lesion depth with Pearson's correlation coefficient of 78% and was highly significant ($p<0.0001$) up to a lesion depth of about 2 mm. Beyond 2 mm, the relationship lost its significance as fNADH values plateaued.

In some embodiments, a system to image ablated and unablated tissue comprises an ultra-violet (UV) laser light source; an inflatable balloon catheter, containing a UV laser guide, and an image guide; an external fluorescence camera, coupled to the catheter; a computer with display, coupled to the camera; and imaging software.

In some embodiments, the catheter further comprises a guide wire port for catheter navigation; and/or ablation therapy technology, including radiofrequency electrodes, laser ablation capability, or cryoablation capability. In some embodiments, the balloon may be made of a compliant material such as silicone or urethane; optically transparent in the UV range of 330 nm to 370 nm; or optically transparent in the fluorescence light range of 430 nm to 490 nm.

In some embodiments, method of estimating lesion depth may include the steps of acquiring and displaying a nicotinamide adenine dinucleotide hydrogen (NADH) fluorescence data of the tissue; identifying of an area of healthy tissue within the image; normalizing the entire image using the ratio of NADH fluorescence intensity observed at each pixel of the image to that observed in the identified healthy tissue; identifying an area or areas of ablated tissue; and applying an algorithm for correlating the resulting normalized image to lesion depth.

In some embodiments, the correlation algorithm uses data is then a pre-established dataset correlating normalized intensity ratio to lesion depth. In some embodiments, the lesion depth estimate uses the patient's own myocardial NADH fluorescence as a control. In some embodiments, the ablation is performed by using one or more of the following technologies: radiofrequency ablation, laser ablation, or cryoablation. The tissue may be cardiac tissue. In some embodiments, a cross-sectional plot of estimated lesion depth is made along a line indicated by the user. In some embodiments, a 3D plot of estimated lesion depth is made by compiling a series of cross-sectional plots.

In some embodiments, a method of treating atrial fibrillation, the method comprises acquiring and displaying an NADH fluorescence data in a certain area of cardiac tissue, such as the ostium of a pulmonary vein; analyzing lesion depth across the image; identification of healthy cardiac tissue; identification of proper lesions; identification of incomplete lesions, if any; identification of ischemic zones (injured but not necrosed tissue), if any; re-apply ablation therapy where needed, either to fill in identified gaps in lesion lines, or to complete incomplete lesions, or bridge ischemic zones; repeating the above steps, as needed to re-acquire and display the repaired tissue; and repeating the above steps to other areas of the heart, such as the remaining pulmonary veins, other parts of the left atrium, or even specific areas of the right atrium including the superior vena cava.

In some embodiments, a catheter to image ablated endocardial heart muscle tissue, unablated gaps at the pulmonary vein/left atrial junction, and lesion depth having a proximal and distal end comprises an inflatable transparent compliant or non-compliant balloon made of UV transparent material inflated with transparent fluid capable of transmitting light used for displacing surrounding blood to allow visualization of NADH fluorescence at the distal end; an ultra-violet illumination device for exciting mitochondrial NADH of the pulmonary vein and left atrial tissue using UV light transmittable fibers at the distal end; a micro fiberscope for detecting NADH fluorescence from the illuminated pulmonary vein and left atrial tissue at the distal end; a fluorescence camera at the proximal end for creating an image from the detected NADH fluorescence, coupled to the micro fiberscope, that includes a 460 nm+/−25 nm band-pass filter to detect the NADH fluorescence from the illuminated pulmonary vein and left atrial tissue captured by the micro fiberscope, wherein the detected fluorescence data shows the physiology of the lesion site having a dark appearance due to lack of fluorescence, gaps having a light appearance due to normal fluorescence, and any ischemic tissue having a brighter halo type appearance surrounding the lesion site; and a module for determining the depth of the lesion site along a line across the length of the lesion site by plotting the detected fluorescence intensity along the line; wherein a lowest fluorescence intensity measurement corresponds to the deepest point of an lesion site and the highest fluorescence corresponds to unablated tissue.

In some embodiments, the module applies a pixel gray scale ranging from completely black to completely white, where 0 is completely black and is the deepest point and 255 is completely white and is the shallowest point, providing 256 (0-255) levels of gray, to create a 2D map of the depth of the lesion site along the line, wherein the 2D map of the depth of ablated tissue is an absolute measurement, with the fNADH signal intensity is normalized to a previously established fNADH/depth grey value scale.

In some embodiments, the 2D map of the depth of the ablated tissue is repeated multiple times along a perpendicular line across the width of the lesion site each of the 2D map of depth being parallel to the line along the length of the lesion and integrating each of the respective 2D maps of depth of the ablated tissue on the perpendicular line reconstructing a 3D image of the depth of the ablated tissue.

In some embodiments, the catheter further comprises a guide wire lumen to insert a flexible guide-wire. The camera may be a CCD camera with high quantum efficiency. In some embodiments, the micro fiberscope is an optical imaging bundle. In some embodiments, the UV illumination is provided by a laser source at between 330 and 370 nm, and more particularly at 355 nm. In some embodiments, the UV illumination fibers tip is covered with a diverging lens to refract and spread the UV light.

In some embodiments, a method for acquiring a real time image of ablated endocardial heart muscle tissue, unablated gaps at the pulmonary vein and left atrial junction and lesion depth, comprises an inflatable transparent compliant balloon made of UV transparent material inflated with transparent fluid capable of transmitting light used for displacing surrounding blood to allow visualization of NADH fluorescence at the distal end; illuminating with a ultra-violet light for exciting mitochondrial NADH of the pulmonary vein and left atrial tissue; detecting NADH fluorescence from the illuminated pulmonary vein and left atrial tissue using optical imaging bundle; creating an image with a fluorescence camera by filtering the detected NADH fluorescence with 460 nm band-pass filter; wherein the detected fluorescence data shows the physiology of the lesion site having a dark appearance due to lack of fluorescence, gaps having a light appearance due to normal fluorescence, and any ischemic tissue having a brighter halo type appearance surrounding the lesion site; and a module for determining the depth of the lesion site along a line across the length of the lesion site by plotting the detected fluorescence intensity along the line; wherein a lowest fluorescence intensity measurement corresponds to the deepest point of an lesion site and the highest fluorescence corresponds to unablated tissue. In some embodimetns, the module applies a pixel gray scale ranging from completely black to completely white, where 0 is completely black and is the deepest point and 255 is completely white and is the shallowest point, providing 256 (0-255) levels of gray, to create a 2D map of the depth of the lesion site along the line, wherein the 2D map of the depth of ablated tissue is an absolute measurement, with the fNADH signal intensity is normalized to a previously established fNADH/depth grey value scale. In some embodiments, the 2D map of the depth of the ablated tissue is repeated multiple times along a perpendicular line across the width of the lesion site each of the 2D map of depth being parallel to the line along the length of the lesion and integrating each of the respective 2D maps of depth of the ablated tissue on the perpendicular line reconstructing a 3D image of the depth of the ablated tissue. In some embodiments, the illumination, imaging and producing are performed while a radio frequency, cryoablation or laser catheter is used to ablate the tissue. In some embodiments, the illumination and imaging are performed using a fiber optic waveguide coupled to a tip of the lumen catheter, the fiber optic waveguide delivers ultraviolet light from the ultraviolet light source to the illuminated tissue. In some embodiments, the ablation is performed by using one of a radio frequency catheter, cryo-ablation catheter, or laser ablation catheter.

In some embodiments, a system comprises a catheter having a distal and proximal end to image ablated pulmonary vein and left atrial heart tissue and unablated gaps, comprising an inflatable compliant or non-compliant balloon inflated with transparent fluid for displacing surrounding blood to allow visualization of NADH fluorescence at the distal end; an ultra-violet illumination device for illuminating the tissue at the distal end; and a micro fiberscope detecting the illuminated tissue at the distal end; a fluorescence camera at the proximal end for creating a 2D image, coupled to the fiberscope, that includes a filter that is configured to pass ultra-violet radiation from the illuminated tissue captured by the fiberscope; wherein the detected 2D image shows the lesion site having a dark appearance due to lack of fluorescence, gaps having a light appearance due to normal fluorescence, and any ischemic tissue having a brighter halo type appearance surrounded the lesion site; an ablation device for ablating heart tissue at the distal end based on the detected 2D image; and a module for determining the depth of the lesion site along a line across the length of the lesion site by plotting the detected fluorescence intensity along the line, wherein a lowest fluorescence intensity measurement corresponds to the deepest point of an lesion site and the highest fluorescence corresponds to unablated tissue. In some embodiments, the module applies a pixel gray scale ranging from completely black to completely white, where 0 is completely black and is the deepest point and 255 is completely white and is the shallowest point, providing 256 (0-255) levels of gray, to create a 2D map of the depth of the lesion site along the line. Wherein the 2D map of the depth of ablated tissue is an absolute measurement, with the fNADH signal intensity is normalized to a previously established fNADH/depth grey value scale. In some embodiments, the 2D map of the depth of the ablated tissue is repeated multiple times along a perpendicular line across the width of the lesion site each of the 2D map of depth being parallel to the line along the length of the lesion and integrating each of the respective 2D maps of depth of the ablated tissue on the perpendicular line reconstructing a 3D image of the depth of the ablated tissue. In some embodiments, a display coupled to the external camera illustrates the detected 2D image. In some embodiments, the ablation device is an ablation catheter having a proximal and distal end. In some embodiments, the ablation catheter is a laser delivery catheter, a radio-frequency delivery catheter, or a cryo-ablation catheter.

In some embodiments, a catheter to image ablated epicardial heart muscle tissue and unablated gaps, having a proximal and distal end comprises an ultra-violet illumination device for exciting mitochondrial NADH of the epicardial heart muscle tissue; a fiberscope detecting NADH fluorescence from the illuminated epicardial heart tissue at the distal end; a fluorescence camera at the proximal end for creating an image from the detected NADH fluorescence, coupled to the fiberscope, that includes a 460 nm band-pass filter to detect the NADH fluorescence captured by the fiberscope; wherein the detected 2D image shows the lesion site having a dark appearance due to lack of fluorescence, gaps having a light appearance due to normal fluorescence, and any ischemic tissue having a brighter halo type appearance surrounded the lesion site, a module for determining the depth of the lesion site along a line across the length of the lesion site by plotting the detected and measured fluorescence intensity along the line; wherein a lowest fluorescence intensity measurement corresponds to the deepest point of an lesion site and the highest fluorescence corresponds to unablated tissue. In some embodiments, the module applies a pixel gray scale ranging from completely black to completely white, where 0 is completely black and is the deepest point and 255 is completely white and is the shallowest point, providing 256 (0-255) levels of gray, to create a 2D map of the depth of the lesion site along the line. Wherein the 2D map of the depth of ablated tissue is an absolute measurement, with the fNADH signal intensity is normalized to a previously established fNADH/depth grey value scale. In some embodiments, the 2D map of the depth of the ablated tissue is repeated on a perpendicular line across the width of the lesion site parallel to the line along the length of the lesion and integrating each of the respective depths of the ablated tissue on the perpendicular line reconstructing a 3D image of the depth of the ablated tissue.

In some embodiments, a catheter having a proximal and distal end to image ablated epicardial heart muscle tissue and unablated gaps, comprises an ultra-violet illumination device for exciting mitochondrial NADH of the epicardial heart muscle tissue at the distal end; a fluorescence camera at the distal end that includes a 460 nm band-pass filter to detect the NADH fluorescence from the illuminated epicardial heart muscle tissue for creating an image from the detected NADH fluorescence; wherein the detected fluorescence data shows the physiology of the lesion site having a dark appearance due to lack of fluorescence, gaps having a light appearance due to normal fluorescence, and any ischemic tissue having a brighter halo type appearance surrounded the lesion site; and a module for determining the depth of the lesion site along a line across the length of the lesion site by plotting the detected and measured fluorescence intensity along the line; wherein a lowest fluorescence intensity measurement corresponds to the deepest point of an lesion site and the highest fluorescence corresponds to unablated tissue. In some embodiments, the module applies a pixel gray scale ranging from completely black to completely white, where 0 is completely black and is the deepest point and 255 is completely white and is the shallowest point, providing 256 (0-255) levels of gray, to create a 2D map of the depth of the lesion site along the line. Wherein the 2D map of the depth of ablated tissue is an absolute measurement, with the fNADH signal intensity is normalized to a previously established fNADH/depth grey value scale. In some embodiments, the 2D map of the depth of the ablated tissue is repeated on a perpendicular line across the width of the lesion site parallel to the line along the length of the lesion and integrating each of the respective depths of the ablated tissue on the perpendicular line reconstructing a 3D image of the depth of the ablated tissue.

As noted above, the present systems and methods provide for high quality and verifiable lesions, which can be at least one aspect to the success of the ablation procedure and avoidance of recurrence. Quality lesions may be of adequate depth and cause cell necrosis completely from the endocardial surface to the epicardial surface of the heart (i.e. transmural) while minimizing damage to the non-cardiac structures beyond. The presently disclosed systems and methods provide feedback as to the extent of cell injury caused by the ablation and actually verify the integrity of a lesion. The presently disclosed embodiments overcome at least some of the problems of known technologies by addressing the lack of lesion-quality feedback by providing lesion visualization as well as depth-of-lesion information to the physician at the time of the procedure. This information should prove useful in forming and verifying proper lesions, reduce fluoroscopy time, and reduce the rate of arrhythmia occurrence, thereby improving outcomes and reducing costs.

According to embodiments, systems and methods of the present disclosure provide real-time, direct visualization of lesions during ablation and gaps using NADH fluorescence. The presently disclosed systems and methods work by detecting the contrast in fluorescence between non-viable ablated and viable myocardium. The present disclosure provides depth-of-lesion information to the physician at real-time, at the time of the procedure.

According to some aspects of the present disclosure, the disclosed systems and methods can be used to determine lesion depth based on the pixel intensity obtained after ablating the tissue and imaging the tissue with a fNADH system. The assessment of ablated lesion depth can be provided by correlating the image intensity provided by the fNADH system to the lesion depth. Which means, the correlated depth data can be integrated into a 3D reconstruction of the lesion(s) giving the physician timely feedback about lesion geometry and quality.

According to some aspects of the present disclosure, there is provide a method for determining a depth of a lesion site that includes illuminating a heart tissue having a lesion site; obtaining a mitochondrial nicotinamide adenine dinucleotide hydrogen (NADH) fluorescence intensity from the illuminated heart tissue along a first line across the lesion site; creating a 2-dimensional (2D) map of the depth of the lesion site along the first line based on the NADH fluorescence intensity; and determining a depth of the lesion site at a selected point along the first line from the 2D map, wherein a lower NADH fluorescence intensity corresponds to a greater depth in the lesion site and a higher NADH fluorescence intensity corresponds to an unablated tissue.

In some embodiments, the method further comprises forming the lesion site in the heart tissue by ablation. The step of obtaining may comprise detecting the NADH fluorescence from the illuminated tissue; creating a digital image of the lesion site from the NADH fluorescence, the digital image comprising a plurality of pixels; and determining a NADH fluorescence intensity of the plurality of pixels along the line across the lesion site. In some embodiments, the method may further include distinguishing the lesion site and a healthy tissue in the digital image based on an amount of the NADH fluorescence from the lesion site and the healthy tissue; normalizing the digital image based on the NADH fluorescence intensity of pixels representative of the healthy tissue.

In some embodiments, the step of detecting comprises filtering the NADH fluorescence through a bandpass filter of between about 435 nm and 485 nm. In some embodiments, the healthy tissue has a lighter appearance and the lesion site has a darker appearance. The step of creating may comprise plotting the NADH fluorescence intensity along the line across the lesion site to create the 2D map of depth of the lesion site.

In some embodiments, the method further includes obtaining a NADH fluorescence intensity from the illuminated heart tissue along a second line across the lesion site; creating a 2D map of the depth of the lesion site along the second line based on the NADH fluorescence intensity; constructing a 3-dimensional (3D) image of the lesion site from the 2D map along the first line and the 2D map along the second line. In some embodiments, the steps of obtaining, creating and determining may be repeated multiple times along a perpendicular line across a width of the lesion site, each of the 2D maps of the depth being parallel to the first line along the length of the lesion site; and integrating each of the respective 2D maps of the depth of the lesion site on a perpendicular line to reconstruct a 3D image of the depth of the lesion site.

The step of determining may comprise applying a pixel gray scale ranging from completely black to completely white. The method may be used to analyze epicardial tissue, endocardial tissue, atrial tissue, and ventricular tissue.

In some embodiments, the illuminating step comprises illuminating the heart tissue with a laser generated UV light, wherein the laser generated UV light may have a wavelength of about 300 nm to about 400 nm.

According to some aspects of the present disclosure, there is provided a system for imaging heart tissue that includes an illumination device configured to illuminate a tissue having a lesion site to excite mitochondrial nicotinamide adenine dinucleotide hydrogen (NADH) in the tissue; an imaging device configured to detect NADH fluorescence from the illuminated tissue; and a controller in communication with the imaging device, the controller being programmed to obtain a NADH fluorescence intensity from the illuminated tissue along a first line across the lesion site; create a 2-dimensional (2D) map of the depth of the lesion site along the first line based on the NADH fluorescence intensity; and determine a depth of the lesion site at a selected point along the first line from the 2D map, wherein a lower NADH fluorescence intensity corresponds to a greater depth in the lesion site and a higher NADH fluorescence intensity corresponds to an unablated tissue.

According to some aspects of the present disclosure, there is provided a system for imaging heart tissue that includes a catheter having a distal region and a proximal region; a light source; an optical fiber extending from the light source to the distal region of the catheter to illuminate a tissue having a lesion site in proximity to the distal end of the catheter to excite mitochondrial nicotinamide adenine dinucleotide hydrogen (NADH) in the tissue; an image bundle for detecting a NADH fluorescence from the illuminated tissue; a camera connected to the image bundle, the camera being configured to receive the NADH fluorescence from the illuminated tissue and to generate a digital image of the illuminated tissue, the digital image comprising a plurality of pixels; and a controller in communication with the camera, the controller being configured to determine, from the digital image, a NAHD fluorescence intensity of the plurality of pixels along a first line across the lesion site, create a 2D map of a depth of the lesion site along the first line based on the NADH fluorescence intensity, and determine a depth of the lesion site at a selected point along the first line from the 2D map, wherein a lower NADH fluorescence intensity corresponds to a greater depth in the lesion site and a higher NADH fluorescence intensity corresponds to an unablated tissue Systems, catheter and methods for treating Atrial Fibrillation (AF) are provided. The fluorescence of endogenous NADH (fNADH) in heart tissue is imaged to identify ablated and unablated areas using a balloon guided catheter equipped with UV illumination source and UV capable fiber, a fluorescence capable camera coupled to an imaging bundle and optical band pass filter to detect NADH fluorescence. Gaps between ablated areas can be identified using the fNADH imaging and the gaps can then be ablated. Depth of ablated lesions are predicted using a gray scale display of the fNADH image and additional lesions can be delivered at lesions of inadequate depth. The imaging can be performed during the ablation procedure and does not require additional chemicals, such as contrast agents, tracers or dyes.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

What is claimed is:

1. A method for determining a depth of a lesion site, the method comprising:
  inserting a catheter and positioning a distal end of the catheter adjacent to a lesion site having two or more lesions in a heart tissue and at least one interlesion gap, wherein the catheter includes one or more optical fibers such that a distal end of the one or more optical fibers extends to the distal end of the catheter and a proximal end of the one or more optical fibers is connected to a light source and an imaging device;
  illuminating the heart tissue having the lesion site with the light source;
  detecting intensity of a mitochondrial nicotinamide adenine dinucleotide hydrogen (NADH) fluorescence from the illuminated tissue;
  creating a digital image of the detected intensity of NADH fluorescence of the lesion site, wherein the digital image of the detected intensity of NADH fluorescence of the lesion site comprises information about a depth and a shape of the two or more lesions and information about the at least one interlesion gap;

analyzing the digital image of the detected intensity of NADH fluorescence of the lesion site to extract the information about the depth and shape of the two or more lesion sites and of the at least one interlesion gap by creating a plurality of 2-dimensional (2D) maps of the lesion site along a plurality of lines across the digital image of the detected NADH fluorescence intensity of the lesion site;

constructing a 3-dimensional (3D) image of the depth and shape of the two or more lesions and of the at least one interlesion gap of the lesion site in the digital image from the plurality of 2D maps along the plurality of lines; and displaying on a display the 3D image of the depth and shape of the two or more lesions and of the at least one interlesion gap of the lesion site to allow for adjustment to the depth and shape of the lesion site.

2. The method of claim 1 further comprising forming the lesion site in the heart tissue by ablation.

3. The method of claim 2 wherein the digital image comprises a plurality of pixels; and wherein detecting a NADH fluorescence intensity of the plurality of pixels occurs along the line across the lesion site.

4. The method of claim 3 further comprising:
distinguishing the lesion site and a healthy tissue in the digital image based on an amount of the NADH fluorescence from the lesion site and the healthy tissue; and
normalizing the digital image based on the NADH fluorescence intensity of pixels representative of the healthy tissue.

5. The method of claim 4, wherein the healthy tissue has a lighter appearance and the lesion site has a darker appearance.

6. The method of claim 3, wherein the step of detecting comprises filtering the NADH fluorescence through a bandpass filter of between about 435 nm and 485 nm.

7. The method of claim 1 wherein the step of creating comprises plotting the NADH fluorescence intensity along the line across the lesion site to create the 2D map of depth of the lesion site.

8. The method of claim 1, wherein the plurality of lines across the digital image for creating each of the 2D maps of the depth being parallel to each other along the length of the lesion site; and integrating each of the respective 2D maps of the depth of the lesion site on a perpendicular line to reconstruct the 3D image of the depth and shape of the lesion site.

9. The method of claim 1, wherein the step of creating comprises applying a pixel gray scale ranging from completely black to completely white.

10. The method of claim 1, wherein the heart tissue is selected form the group consisting of epicardial tissue, endocardial tissue, atrial tissue, and ventricular tissue.

11. The method of claim 1, wherein the illuminating step comprises illuminating the heart tissue with a laser generated UV light.

12. The method of claim 11, wherein the laser generated UV light has a wavelength of about 300 nm to about 400 nm.

13. The method of claim 1, wherein the plurality of lines are parallel.

14. A system for imaging heart tissue comprising:
a catheter having a distal end configured to be positioned adjacent to a lesion site having two or more lesions in a heart tissue and at least one interlesion gap, wherein the catheter includes one or more optical fibers such that a distal end of the one or more optical fibers extends to the distal end of the catheter;

an illumination device coupled to a proximal end of the optical fibers and configured to illuminate a tissue having a lesion site to excite mitochondrial nicotinamide adenine dinucleotide hydrogen (NADH) in the tissue;

an imaging device coupled to the proximal end of the optical fibers and configured to detect NADH fluorescence from the illuminated tissue;

a controller in communication with the imaging device, the controller being programmed to
analyze an image from the imaging device and to obtain a NADH fluorescence intensity from the illuminated tissue,
create a digital image of the NADH fluorescence intensity of the lesion site, wherein the digital image of the detected intensity of NADH fluorescence of the lesion site comprises information about a depth and shape of the two or more lesions and information about the at least one interlesion gap;
analyze the digital image of the detected intensity of NADH fluorescence of the lesion site to extract the information about the depth and shape of the two or more lesions and information about the at least one interlesion gap by creating a plurality of 2-dimensional (2D) maps of the depth of the lesion site along the plurality of lines across the digital image of the lesion site based on the detected NADH fluorescence intensity; and
construct a 3-dimensional (3D) image of the depth and shape of the two or more lesions and of the at least one interlesion gap of the lesion site in the digital image from the plurality of 2D maps along the plurality of lines; and a display configured to display the 3D image of the depth and shape of the two or more lesions and of the at least one interlesion gap of the lesion site to allow for adjustments to the depth and shape of the lesion site of the heart tissue.

15. The system of claim 14, wherein the illumination device is a UV laser.

16. The system of claim 15, wherein the controller is further programmed to receive the detected NADH fluorescence from the illuminated tissue from the imaging device; create a digital image of the lesion site from the NADH fluorescence, the digital image comprising a plurality of pixels; and determine a NADH fluorescence intensity of the plurality of pixels along the line across the lesion site.

17. The system of claim 14, wherein the imaging device comprises a camera and a fiberscope extending from the camera to the tissue being illuminated.

18. The system of claim 17, wherein the imaging device further incudes a bandpass filter of between about 435 nm and 485 nm disposed between the camera and the fiberscope.

19. The system of claim 14, wherein the plurality of lines are parallel.

20. A system for imaging tissue comprising:
a catheter having a distal region and a proximal region;
a light source;
an optical fiber extending from the light source to the distal region of the catheter to illuminate a tissue having a lesion site having two or more lesions and at least one interlesion gap in proximity to the distal region of the catheter to excite mitochondrial nicotinamide adenine dinucleotide hydrogen (NADH) in the tissue;

an image bundle for detecting a NADH fluorescence from the illuminated tissue;

a camera connected to the image bundle, the camera being configured to receive the NADH fluorescence from the illuminated tissue and to generate a digital image of a NADH fluorescence intensity from the illuminated tissue, the digital image comprising a plurality of pixels;

a controller in communication with the camera, the controller being configured to determine, from the digital image, a NAHD fluorescence intensity of the plurality of pixels along a plurality of lines across the digital image of the lesion site, the NADH fluorescence intensity being indicative of a depth and shape of the two or more lesions and information about the at least one interlesion gap, create a plurality of 2D maps of the depth and shape of the two or more lesions and information about the at least one interlesion gap along the plurality of lines across the digital image of the lesion site based on the NADH fluorescence intensity, and construct a 3-dimensional (3D) image of the depth and shape of the two or more lesions and of the at least one interlesion gap of the lesion site in the digital image from the plurality of 2D maps along the plurality of lines; and a display configured to display the 3D image of the depth and shape of the two or more lesions and of the at least one interlesion gap of the lesion site, wherein a user adjusts the depth and shape of the two or more lesions and of the at least one interlesion gap of the lesion site based on the displayed depth and shape of the two or more lesions and of the at least one interlesion gap of the lesion site until a desired depth and shape of the two or more lesions and of the at least one interlesion gap of the lesion site is achieved.

21. The system of claim 20, wherein the plurality of lines are parallel.

* * * * *